(12) United States Patent
Fauth et al.

(10) Patent No.: US 9,775,720 B2
(45) Date of Patent: Oct. 3, 2017

(54) FUSION CAGE

(71) Applicant: COORSTEK MEDICAL LLC, Providence, UT (US)

(72) Inventors: Andrew R. Fauth, North Logan, UT (US); Dylan M. Hushka, Niwot, CO (US); Nicholas Slater, Chandler, AZ (US); Joshua A. Butters, Chandler, AZ (US); Brad A. Niese, Chandler, AZ (US); Mark J. Mooradian, San Diego, CA (US)

(73) Assignee: CoorsTek Medical LLC, Providence, UT (US)

( * ) Notice: Subject to any disclaimer, the term of this patent is extended or adjusted under 35 U.S.C. 154(b) by 0 days.

(21) Appl. No.: 15/284,491

(22) Filed: Oct. 3, 2016

(65) Prior Publication Data
US 2017/0020684 A1   Jan. 26, 2017

Related U.S. Application Data

(63) Continuation of application No. 14/207,048, filed on Mar. 12, 2014, now Pat. No. 9,456,908.

(60) Provisional application No. 61/777,666, filed on Mar. 12, 2013.

(51) Int. Cl.
*A61F 2/44* (2006.01)
*A61B 17/86* (2006.01)
*A61F 2/30* (2006.01)

(52) U.S. Cl.
CPC .......... *A61F 2/4455* (2013.01); *A61B 17/86* (2013.01); *A61F 2/44* (2013.01); *A61F 2/447* (2013.01); *A61F 2/4465* (2013.01); *A61F 2002/3052* (2013.01); *A61F 2002/3055* (2013.01); *A61F 2002/30387* (2013.01); *A61F 2002/30403* (2013.01); *A61F 2002/30507* (2013.01); *A61F 2002/30515* (2013.01); *A61F 2002/30523* (2013.01); *A61F 2002/30579* (2013.01); *A61F 2002/30611* (2013.01); *A61F 2002/30841* (2013.01); *A61F 2002/30883* (2013.01); *A61F 2002/30884* (2013.01)

(58) Field of Classification Search
CPC .................................................... A61F 2/4455
See application file for complete search history.

(56) References Cited

U.S. PATENT DOCUMENTS

| 4,863,476 | A | | 9/1989 | Shepperd |
| 5,290,312 | A | * | 3/1994 | Kojimoto ............... A61F 2/44 606/247 |
| 5,782,832 | A | | 7/1998 | Larsen et al. |
| 6,102,950 | A | | 8/2000 | Vaccaro |
| 6,179,873 | B1 | | 1/2001 | Zientek |

(Continued)

FOREIGN PATENT DOCUMENTS

| AU | 2013206287 | 7/2013 |
| EP | 1374809 | 1/2004 |

(Continued)

*Primary Examiner* — Andrew Yang
(74) *Attorney, Agent, or Firm* — David L. Stott

(57) ABSTRACT

A system comprising a fusion cage and at least one engagement member is provided. The fusion cage includes a first member and a second member. The engagement member is configured to retain the first and second members in an expanded state while simultaneously fixing the fusion case to adjacent vertebrae.

15 Claims, 28 Drawing Sheets

(56) References Cited

U.S. PATENT DOCUMENTS

| | | |
|---|---|---|
| 6,296,665 B1 | 10/2001 | Strnad et al. |
| 6,299,644 B1 | 10/2001 | Vanderschot |
| 7,500,992 B2 | 3/2009 | Li |
| 7,544,208 B1 | 6/2009 | Mueller et al. |
| 7,674,296 B2 * | 3/2010 | Rhoda ............ A61F 2/44 623/17.11 |
| 7,799,081 B2 | 9/2010 | McKinley |
| 7,887,588 B2 | 2/2011 | Rapp |
| 7,892,286 B2 * | 2/2011 | Michelson ............ A61F 2/4455 623/17.15 |
| 8,100,972 B1 | 1/2012 | Bruffey et al. |
| 8,105,381 B2 | 1/2012 | Marnay et al. |
| 8,128,700 B2 | 3/2012 | Delurio et al. |
| 8,142,508 B1 | 3/2012 | Bruffey et al. |
| 8,252,054 B2 | 8/2012 | Greenhalgh et al. |
| 8,357,181 B2 | 1/2013 | Lange et al. |
| 8,377,140 B2 | 2/2013 | DeFalco et al. |
| 8,382,843 B2 | 2/2013 | Laurence et al. |
| 8,403,990 B2 | 3/2013 | Dryer et al. |
| 8,409,286 B2 | 4/2013 | Mckay |
| 8,460,388 B2 | 6/2013 | Kirwan et al. |
| 8,491,653 B2 | 7/2013 | Zucherman et al. |
| 8,512,409 B1 | 8/2013 | Mertens et al. |
| 8,523,946 B1 | 9/2013 | Swann |
| 8,540,769 B2 | 9/2013 | Janowski et al. |
| 8,540,770 B2 | 9/2013 | Woodburn, Sr. et al. |
| 8,574,300 B2 | 11/2013 | Mcmanus et al. |
| 2003/0074064 A1 | 4/2003 | Gerbec et al. |
| 2004/0059271 A1 | 3/2004 | Berry |
| 2004/0162618 A1 | 8/2004 | Mujwid et al. |
| 2004/0186569 A1 | 9/2004 | Berry |
| 2004/0254644 A1 | 12/2004 | Taylor |
| 2005/0021144 A1 | 1/2005 | Malberg et al. |
| 2005/0033439 A1 | 2/2005 | Gordon et al. |
| 2005/0113921 A1 | 5/2005 | An et al. |
| 2005/0149193 A1 | 7/2005 | Zucherman et al. |
| 2005/0177235 A1 | 8/2005 | Baynham et al. |
| 2005/0234555 A1 | 10/2005 | Sutton et al. |
| 2006/0004447 A1 | 1/2006 | Mastrorio et al. |
| 2006/0095136 A1 | 5/2006 | McLuen |
| 2006/0212121 A1 | 9/2006 | Ferree |
| 2006/0241770 A1 | 10/2006 | Rhoda et al. |
| 2007/0050033 A1 | 3/2007 | Reo et al. |
| 2007/0123987 A1 | 5/2007 | Bernstein |
| 2007/0250171 A1 | 10/2007 | Bonin |
| 2007/0255407 A1 | 11/2007 | Castleman et al. |
| 2007/0255415 A1 | 11/2007 | Edie et al. |
| 2007/0255421 A1 | 11/2007 | Dickson |
| 2007/0270952 A1 | 11/2007 | Wistrom et al. |
| 2007/0270960 A1 | 11/2007 | Bonin et al. |
| 2008/0009946 A1 | 1/2008 | Douget et al. |
| 2008/0033440 A1 | 2/2008 | Moskowitz et al. |
| 2008/0132949 A1 | 6/2008 | Aferzon et al. |
| 2008/0140207 A1 | 6/2008 | Olmos et al. |
| 2008/0167720 A1 | 7/2008 | Melkent |
| 2008/0177333 A1 | 7/2008 | Ferguson |
| 2009/0216331 A1 | 8/2009 | Grotz et al. |
| 2009/0234456 A1 | 9/2009 | Nycz |
| 2010/0076559 A1 | 3/2010 | Bagga et al. |
| 2010/0082109 A1 | 4/2010 | Greenhalgh et al. |
| 2010/0204737 A1 | 8/2010 | Bae et al. |
| 2011/0178599 A1 | 7/2011 | Brett |
| 2013/0211526 A1 | 8/2013 | Alheidt et al. |
| 2014/0163682 A1 * | 6/2014 | Lott ............ A61F 2/4425 623/17.15 |

FOREIGN PATENT DOCUMENTS

| | | |
|---|---|---|
| EP | 1634549 | 3/2006 |
| JP | 2010051651 | 3/2010 |
| WO | WO9000037 | 1/1990 |
| WO | WO0156513 | 8/2001 |
| WO | WO0170139 | 9/2001 |
| WO | WO2006110443 | 10/2006 |
| WO | WO2007098288 | 8/2007 |
| WO | WO2008044057 | 4/2008 |
| WO | WO2011142761 | 11/2011 |
| WO | WO2013008111 | 1/2013 |
| WO | WO2013025448 | 2/2013 |

* cited by examiner

FUSION CAGE

CROSS-REFERENCE TO RELATED APPLICATIONS

The present application is a continuation of U.S. patent application Ser. No. 14/207,048, filed Mar. 12, 2014, which claims the benefit of U.S. Provisional Application No. 61/777,666, filed Mar. 12, 2013.

TECHNICAL FIELD

The present disclosure relates to orthopedic implants. More specifically, but not exclusively, the present disclosure relates to fusion cages placed between adjacent vertebral bodies at any spinal level.

RELEVANT TECHNOLOGY

It is desirable to insert a fusion cage into a patient's body such that the fusion cage defines a small footprint during insertion. The fusion cage may be expanded to define a larger footprint or greater height once it is placed between the vertebral bodies. Fusion cages are often fixed to neighboring bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

Figure 1:
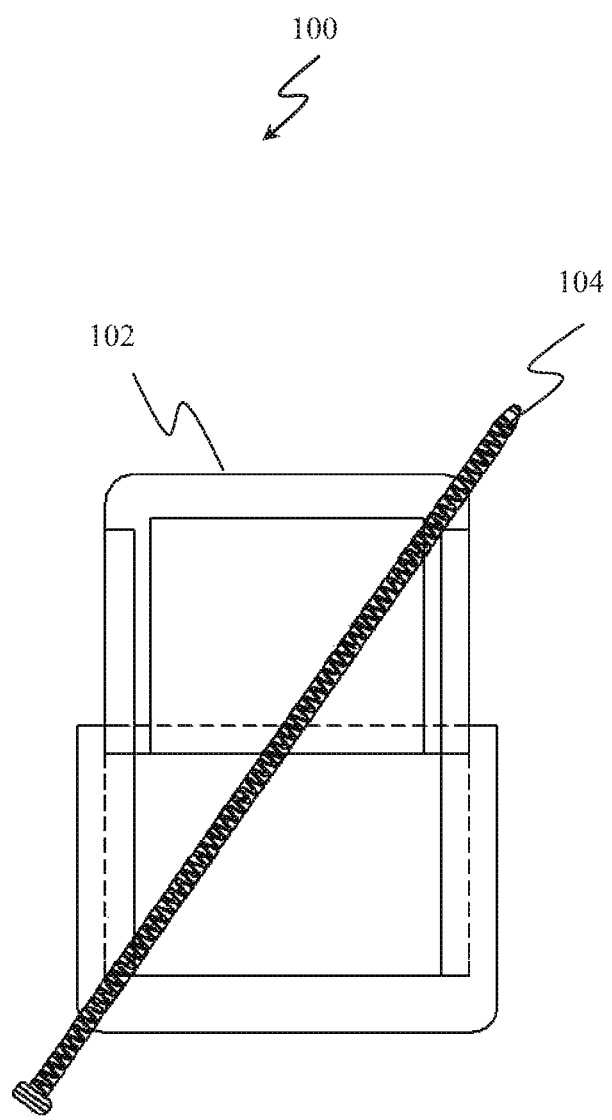
FIG. 1 is a front view of system 100.
Figure 1A:
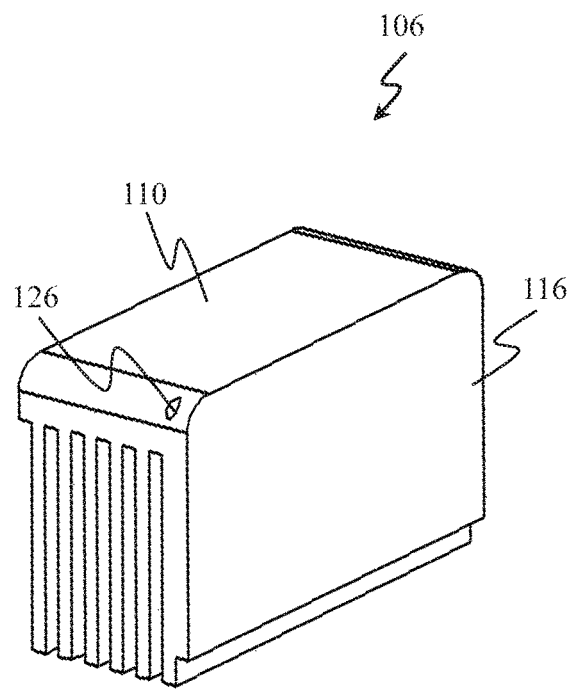
FIG. 1A is a isometric view of a first member.
Figure 1B:
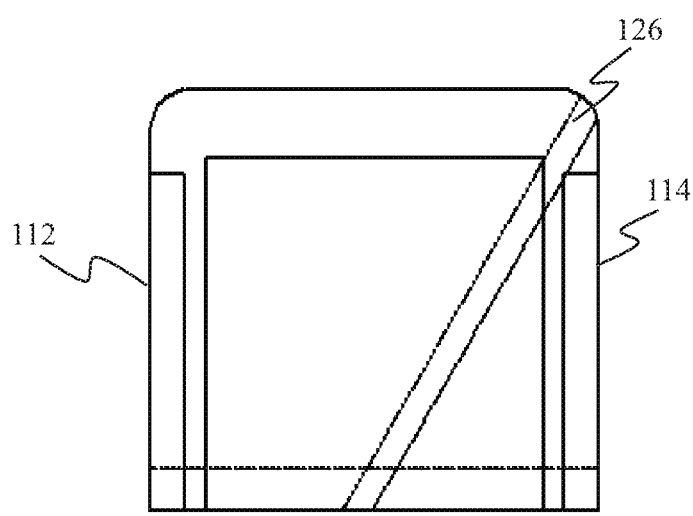
FIG. 1B is a front view of the first member of FIG. 1A.
Figure 1C:
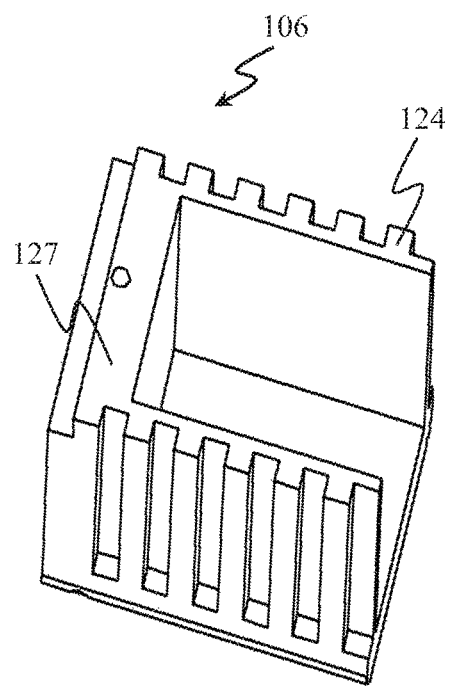
FIG. 1C is bottom view of the first member of FIG. 1A.
Figure 1D:
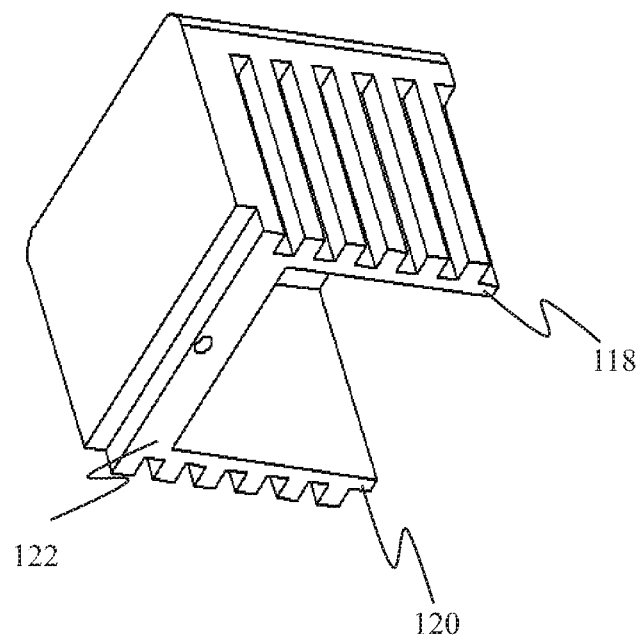
FIG. 1D is a perspective view of the first member of FIG. 1A.
Figure 1E:
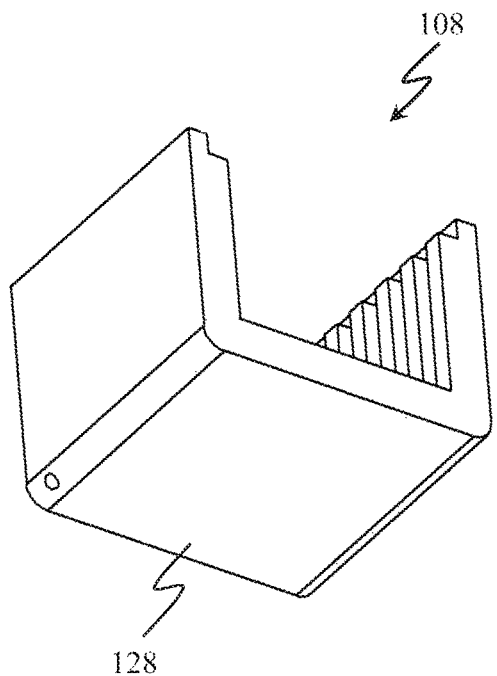
FIG. 1E is a bottom view of a second member.
Figure 1F:
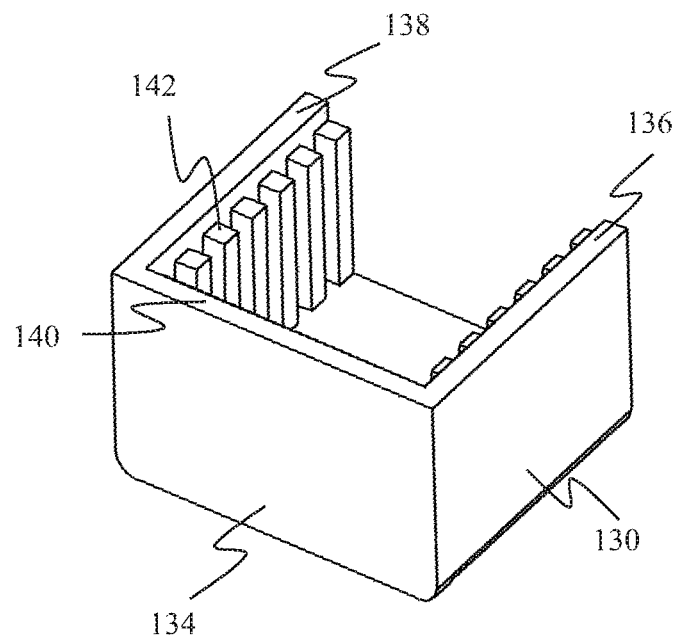
FIG. 1F is isometric view of the second member of FIG. 1E.
Figure 1G:
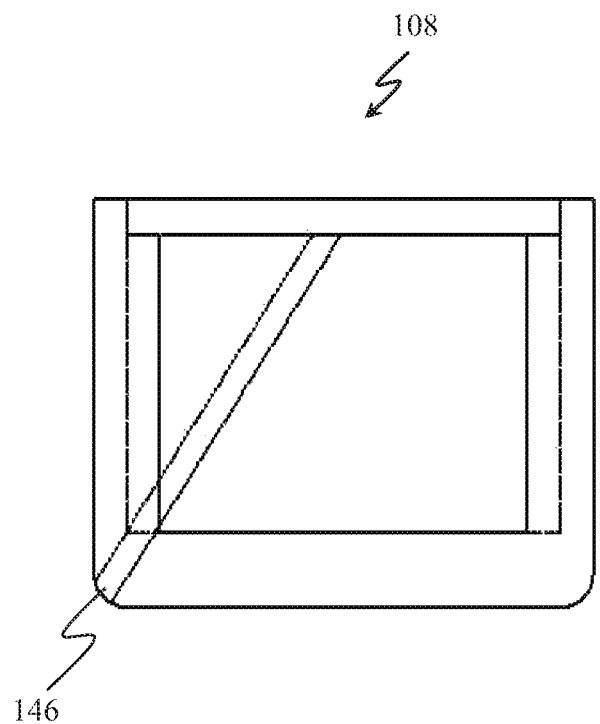
FIG. 1G is a front view of the second member of FIG. 1E.
Figure 1H:
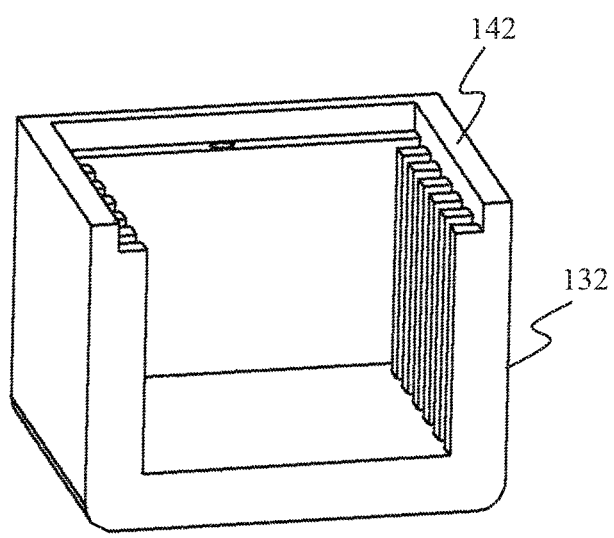
FIG. 1H is another view of the second member of FIG. 1E.

The present invention relates to fusion cages placed into the spine at any spinal level. The systems and methods described herein may be readily adapted for other medical devices. The following description illustrates the principles of the invention, which may be applied in various ways to provide many different alternative embodiments. This description is not meant to limit the inventive concepts in the appended claims. The disclosure may relate to fusion cages employed in spinal fusion procedures. The following description illustrates principles, which may be applied in various ways to provide many different alternative embodiments. This description is not meant to limit the inventive concepts in the appended claims.

The present technology may be employed in spinal fusion procedures wherein two vertebral bodies are joined together to maintain foraminal height by replacing the spinal disc whenever required and implanting the fusion cages between the vertebral bodies. While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. In addition, one of ordinary skill in the art will appreciate upon reading and understanding this disclosure that other variations for the technology described herein can be included within the scope of the present technology.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

A system comprising a fusion cage and an engagement member may be provided between two adjacent vertebral bodies. The fusion cage may be received between the two adjacent vertebral bodies in a collapsed position. Thereafter, the fusion cage may be operated such that the fusion cage assumes an expanded position. The engagement member may enable the fusion cage to retain the expanded position and or enable the fusion cage to expand.

The fusion cage may be expanded in a superior inferior direction or in a footprint direction. The fusion cage may remain in the collapsed position before expansion. The fusion cage may be inserted in a patient's body while the fusion cage in the collapsed position. Thereafter, once the fusion cage is located at a position where it may have to support two bodies, such as the two adjacent vertebral bodies, the fusion cage may be expanded. Hence, the fusion cage may have a smaller footprint while it is still being located at the desired location, thereby making a fusion cage implant surgery less traumatic for the patient.

Referring to FIG. 1, a system 100 may be used for providing support between two adjacent vertebral bodies. The system 100 may include a fusion cage 102 and an engagement member 104.

The fusion cage 102 may include a first member 106 or first support means and a second member 108 or second support means. The first member 106 may be an upper portion or top portion of the fusion cage 102 and the second member 108 may be a lower portion or bottom portion of the fusion cage 102. On the other hand, the first member 106 may be a lower portion of the fusion cage 102 and the second member 108 may be an upper portion of the fusion cage 102.

Referring to FIGS. 1A-1D, the first member 106 may include a first support portion 110. The first support portion 110 of the first member 106 may interface with at least a surface of a first vertebral body.

The first member 106 may include three support arms 112, 114 and 116. The support arms 112, 114 and 116 may extend from three edges of the first support portion 110 of the first member 106. The edges from which the support arms 112 and 114 extend may be facing each other. The edge from which the support arm 116 extends may be disposed between the edges from which the support arms 112 and 114 extend. The support arms 112, 114 extend towards a second support portion from the first support portion 110.

Each of the support arms may include interface surfaces. The support arm 112 may have an interface surface 118, the support arm 114 may have an interface surface 120 and the support arm 116 may have an interface surface 122. The interface surfaces 118, 120 and 122 of the support arms 112, 114 and 116 of the first member 106 face away from the first support portion 110.

The support arms 112, 114 and 116 may also include additional surfaces apart from the interface surfaces 118, 120 and 122. Each one of the support arms 112 and 114 may include an anterior surface, a posterior surface, a surface that interfaces a surface of the first support portion 110, an external surface and an internal surface.

The support arm 116 may also include additional surfaces. The support arm 116 may include an anterior surface, a posterior surface, a surface that interfaces the first support portion 110 and a surface that interfaces with a part of the internal surface of the support arm 112 and a surface that interfaces with a part of the internal surface of the support arm 114. The surface that interfaces the first support portion 110 may be facing away from the interface surface 122.

The internal surface of the support arm 112 of the first member 106 may define slots 124. The slots 124 may assume rectangular shape. The slot 124 may have a depth in the lateral direction of the support arm 112. The slots 124 may be configured to receive keys.

Similar slots 124 may be included on one of the surfaces of the support arm 114. Corresponding keys may be present on the support arms of the second member 108 which may be received by the slots 124.

The first member 106 may include a first channel 126. The first channel 126 may have a configuration such that it can accommodate the engagement member 104 either partially or entirely within.

The first channel 126 may have an oblique orientation with respect to the first support portion 110 of the first member 106. The first channel 126 may have internal threads partially or entirely throughout the length of the channel 126.

The first member 106 may further include a step 127. The step 127 may be provided on the interface surfaces 118, 120 and 122 of the support arms 112, 114 and 116 of first support portion 110. The step 127 may be configured such that it provides support to the support arms extending from a second support portion from making movement sideward when the fusion cage 102 is in an expanded position.

The steps 127 may assume a rectangular shape extending throughout the lengths of the support arms 112, 114 and 116 and have a width extending in the inferior direction which may be facing away from the first support portion 110.

Referring to FIGS. 1E-1H, the second member 108 may include a second support portion 128. The second support portion 128 of the second member 108 may interface with at least a surface of a second vertebral body.

The second member 108 may include three support arms 130, 132 and 134. The support arms 130, 132 and 134 may extend from three edges of the second support portion 128 of the second member 108. The edges from which the support arms 130 and 132 extend may be facing opposite to each other. The edge from which the support arm 134 extends may be disposed between the edges from which the support arms 130 and 132 extend. The support arms 130, 132 and 134 may extend towards the first support portion 110 from the second support portion 128.

Each of the support arms may include interface surfaces. The support arm 130 may have an interface surface 136, the support arm 132 may have an interface surface 138 and the support arm 134 may have an interface surface 140. The interface surfaces 136, 138 and 140 of the support arms 130, 132 and 134 of the second member 108 face away from the second support portion 128.

The support arms 120, 122 and 124 may also include additional surfaces apart from the interface surfaces 132, 134 and 136. Each one of the support arms 120 and 122 may include an anterior surface, a posterior surface, a surface that interfaces a surface of the second support portion 120, an external surface and an internal surface.

The support arm 124 may also include additional surfaces. The support arm 124 may include an anterior surface, a posterior surface, a surface that interfaces a surface of the second support portion 128 and a surface that interfaces with a part of the internal surface of the support arm 120 and another surface that interfaces with a part of the internal surface of the support arm 122. The surface that interfaces a surface the second support portion 128 may be facing away from the interface surface 140.

The second member 108 may further include a step 142. The step 142 may be provided on the interface surfaces 136, 138 and 140 of the support arms 130, 132 and 134 of the second support portion 128. The step 142 may be configured such that it provides support to the support arms 112, 114 and 116 from making movement sideward when the fusion cage 102 is in an expanded position.

The steps 142 may assume a rectangular shape extending throughout the lengths of the support arms 130, 132 and 134 and have a width extending in a superior direction which may be facing away from the second support portion 128.

The external surface of the support arm 130 of the second member 108 may include keys 144. A key 144 may assume a rectangular shape. The key 144 may be a rectangular structure extending externally towards the slot 124 present on the support arm 112 of the first member 106 in the lateral direction of the support arm 130. The key 144 may be configured such that the width of the key 144 may be accommodated within the width and the depth of the slot 124. Similar keys 144 may be included on the external surface of the support arm 132.

The second member 108 may include a second channel 146. The second channel 146 may have a configuration such that it can accommodate the engagement member 104 either partially or allow the engagement member 104 to pass through it.

The second channel 146 may have an oblique orientation with respect to the second support portion 128 of the second member 108. The second channel 146 may have internal threads partially or entirely throughout the length of the channel 146.

The engagement member 104 of the system 100 may be configured to provide support to the first member 106 and the second member 108 in an expanded position and may retain the expanded position as long as requirement persists, and may even mechanically engage the fusion cage 102 with the vertebral bodies.

More specifically, the engagement member 104 (or any other engagement member or similar structure described in this disclosure) may serve to provide two functions simultaneously: first, engagement with first and second expanding members (such as members 106 and 108) in an expanded position, and second, engagement (or fixation, such as supplemental fixation) with surrounding tissue or bone (such as a vertebral body adjacent the fusion cage 102, first member 106, and/or second member 108). Since engagement member 104 (or any other engagement member or similar structure) fixes the system 100 in an expanded state while also fixing the system 100 and its associated structures to neighboring bone, the engagement member accomplishes multiple functions with a single (or few) structure(s). By providing fixation of the system in an expanded state and fixation of the system to one or more neighboring bones or vertebrae through a single (or few) structure(s), the engagement member is an improvement over existing systems that otherwise require multiple structures to provide those multiple functions. The multiple structures of other systems leave little remaining internal space within the system 100 for bone graft, cement, biologic material, or other material to be included. By contrast, the current system 100 is an expandable fusion cage having a single engagement member capable of simultaneously locking the cage in the expanded state and locking the cage to adjacent vertebral (or other bone) tissue using supplemental fixation, in such a manner as to increase the volume of the void within the cage for the inclusion of bone graft, biologic material, or bone cement. The inclusion of additional bone graft, biologic material, or bone cement within a spinal fusion cage can help promote bone growth and stronger spinal fusion within the space surrounding an implanted cage or system 100. Thus, clinical outcomes for patients may be improved by the multifunctional engagement members of the present disclosure.

The engagement member 104 may include threads partially or entirely throughout the length of the engagement member 104. The engagement member 104 may be partially or entirely received by the first channel 126 and the second channel 146 in the expanded position of the fusion cage 102. The engagement member 104 may be a screw or any other member which may be used to provide support to the fusion cage 102 in its expanded position.

The engagement member 104 may be received by the channels 126 and 146 by aligning the threads in the channels 126 and 146 with the threads of the engagement member 104. The alignment of the threads in the channels 126 and 146 and the threads of the engagement member 104 ensures secure fastening of the engagement member 104 within the channels 126 and 146.

Figure 1I:
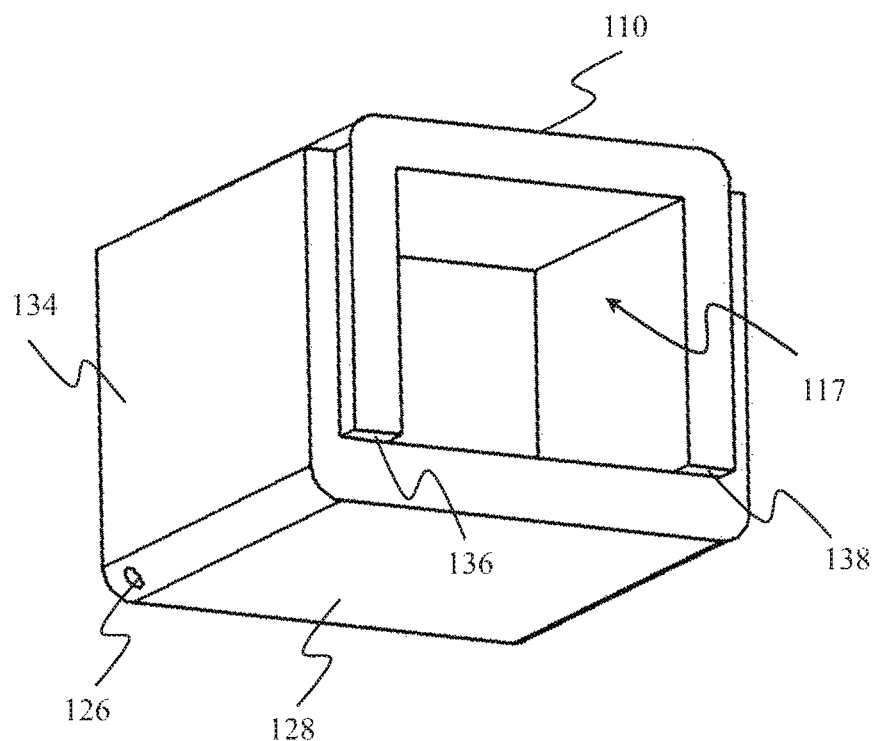
FIG. 1I is an isometric view of a collapsed position of system 100.

Referring to FIG. 1I, the first support portion 110 may be configured such that in a collapsed position, the support arms 112, 114 and 116 extending from the support portion 110 may be disposed between the support arms 130, 132 and 134 extending from the second support portion 128.

In the collapsed position, the external surface of support arms 112 may coincide with the internal surface of the support arm 130. The external surface of support arm 114 may coincide with the internal surface of the support arm 132. The posterior surface of the support arm 116 may coincide with the anterior surface of the support arm 134. The configuration of the support arms 114, 116, 118 and the support arms 130, 132 and 134 in the collapsed position may define a first space 117.

In the collapsed position, slots 124 provided on the external surface of the support arm 112 of the first support portion 110 may be received by the corresponding keys 144 provided on the external surface of the support arm 130 of the second support portion 128. The key 144 may be configured such that the width of the key 144 may be accommodated within the width and the depth of the slot 124. The reception of the keys 144 by the slots 124 ensure that, in the collapsed position, the movement of the first member 106 and the second member 108 is prevented.

The fusion cage 102 may be operated to assume the expanded position by moving one of the first member 106 or the second member 108 in a superior inferior direction. The movement in the superior inferior direction may occur along the longitudinal axis of the slots 124 and keys 144.

While moving the first member 106 or the second member 108 in the superior inferior direction, the distance between the first support portion 110 and the second support portion 128 increases until the keys 144 exit the slots 124.

In the expanded position, a portion of one of the interface surface(s) 118 of the support arm 112 may interface with interface surface 136 of the support arm 130. Similarly, interface surface 120 of the support arm 114 may interface with interface surface 138 of the support arm 132, and interface portion 122 of the support arm 116 may interface with interface surface 140 of the support arm 134.

Once the keys 144 exit the slots 124 while expanding the fusion cage 102, one of the first member 106 or the second member 108 may be moved in a direction orthogonal to the longitudinal axis of the slots 124 and keys 144. By moving the first member 106 or the second member 108 in direction orthogonal to the longitudinal axis of the slots 124 and keys 144, it is ensured that further movement between the first member 106 and the second member 108 is prevented in the expanded position.

In the expanded position, the steps 142 provided on the second member 108 may receive a portion of the external surfaces of the support arms 112 and 114 and a portion of the posterior surface of the support arm 116. The reception of the external surfaces of the support arms 112, 114 and 116 by the steps 142 may prevent the first member 106 from making sideward movement in the expanded position.

Figure 1J:
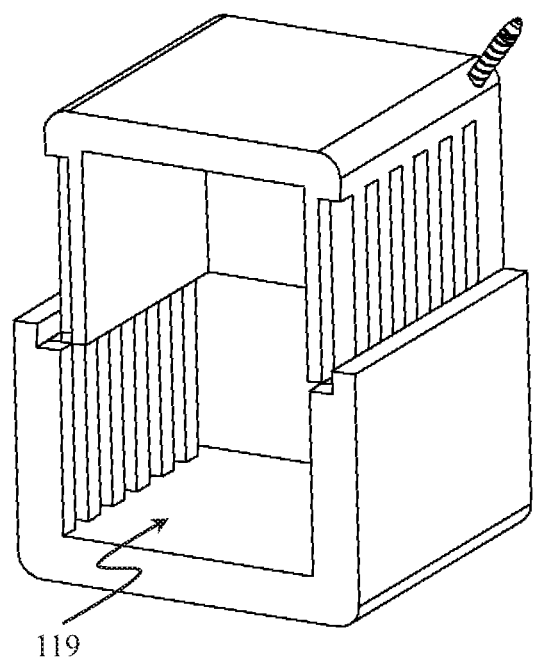
FIG. 1J is an isometric view of an expanded position of system 100.

Referring to FIG. 1J, in the expanded position, the support arms 112, 114, 116, 120, 122 and 124, the first support portion 110 and the second support portion 120 define a second space 119. The second space 119 may be used for insertion of graft material during the spinal fusion process.

Figure 1K:
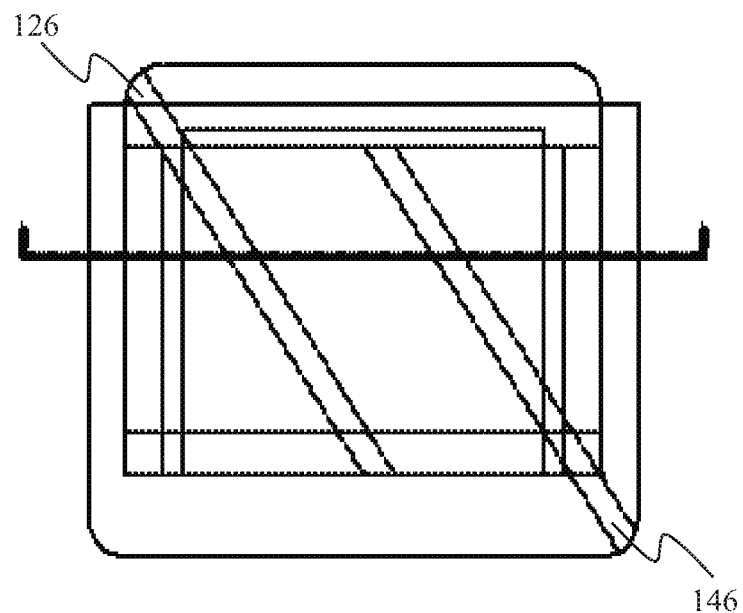
FIG. 1K is front view of a collapsed position of system 100 of FIG. 1I.

Referring to FIG. 1K, in the collapsed position, the first channel 126 and the second channel 146 may be at offset positions. The offset may be obliquely oriented with respect to the first channel 126 and the second channel 146. The offset may further be oriented at a parallel position with respect to the first channel 126 and the second channel 146.

Figure 1L:
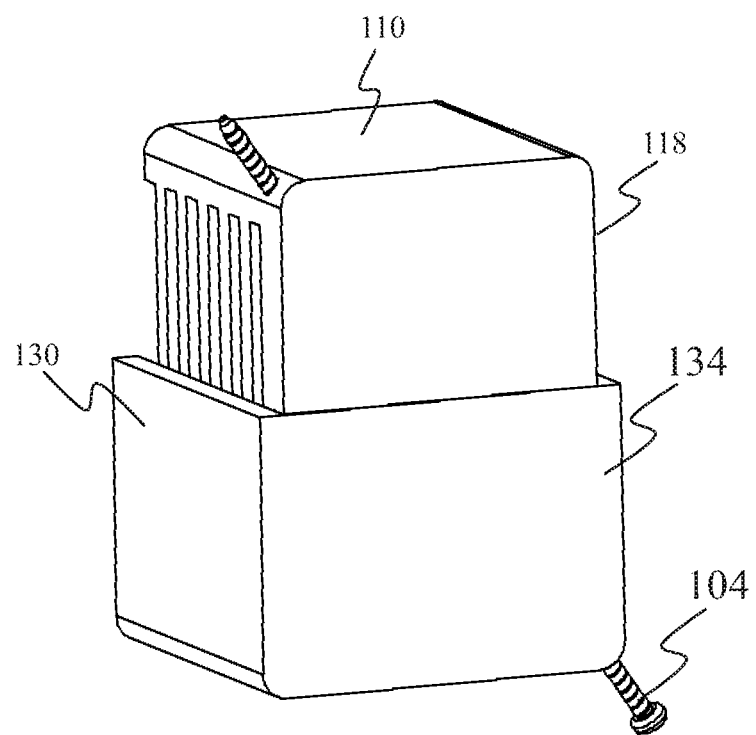
FIG. 1L is a back view of an expanded position of system 100 of FIG. 1J.

Referring to FIG. 1L, in an expanded position, when the first member 106 is moved along the longitudinal axis of the slots 124 and keys 144, the first channel 144 being a part of the first member 106 and the second channel 144 being a part of the second member 108, also move thereby making an alignment.

In an expanded position, the alignment of the first channel 126 with the second channel 146 makes way for the engagement member 104 to be disposed into the channels 126 and 146. When the engagement member 104 is received by the channels 126 and 146, the threads in the channels 126 and 146 aligns with the threads of the engagement member 104. The alignment of the threads in the channels 126 and 146 and the threads of the engagement member 104 ensures secure fastening of the engagement member 104 within the channels 126 and 146.

Figure 2:
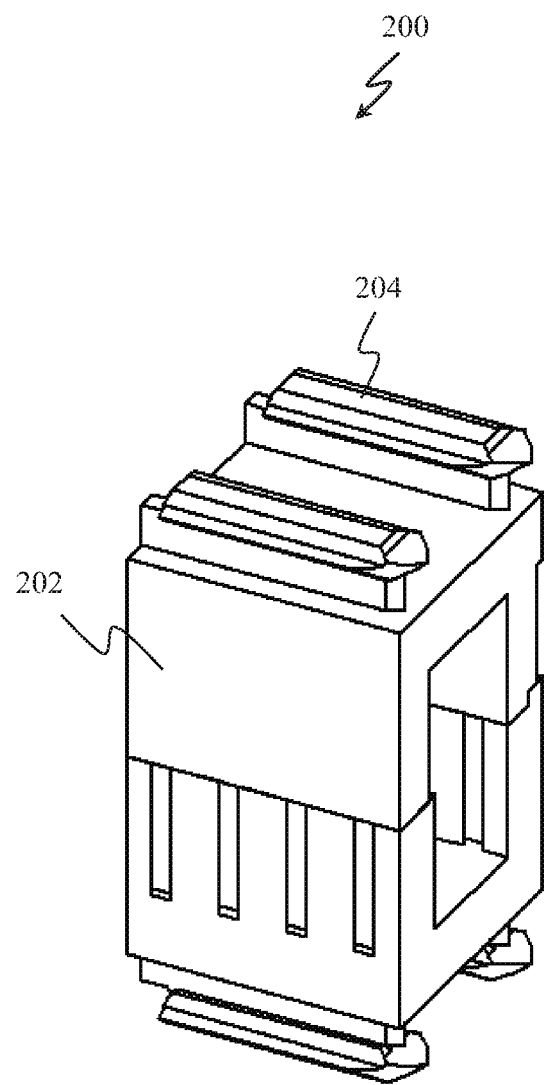
FIG. 2 is a isometric view of system 200.

Referring to FIG. 2, a system 200 may be used for providing support to two adjacent vertebral bodies. The system 200 may include a fusion cage 202 and an engagement member 204.

The fusion cage 202 may include a first member 206 and a second member 208. The first member 206 may be an upper portion of the fusion cage 202 and the second member 208 may be a lower portion of the fusion cage 202. On the other hand, the first member 206 may be a lower portion of the fusion cage 202 and the second member 208 may be an upper portion of the fusion cage 202.

Figure 2A:
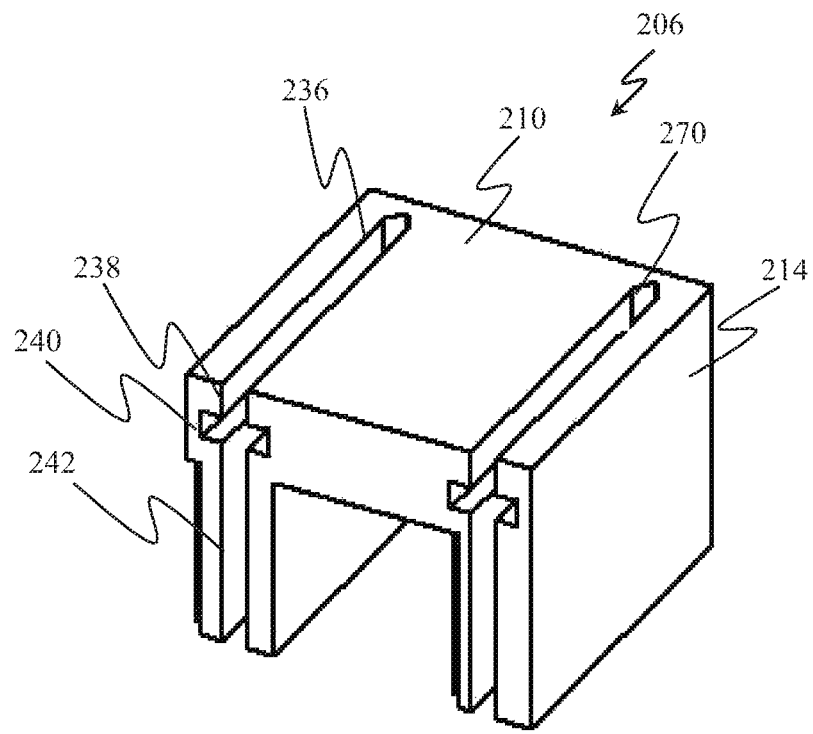
FIG. 2A is an isometric view of a first member of system 200.
Figure 2B:
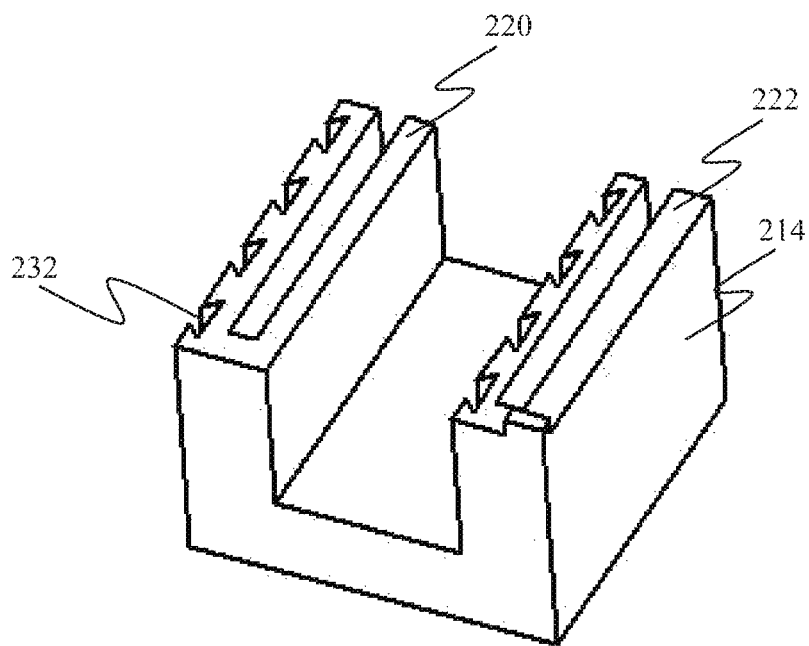
FIG. 2B is a bottom view of the first member of FIG. 2A.

Referring to FIGS. 2A-2B the first member 206 may include a first support portion 210. The first support portion 210 of the first member 206 may interface with at least a surface of a first vertebral body.

The first member 206 may include a pair of support arms 212 and 214. The support arms 212 and 214 may extend from two edges of the first support portion 210 of the first member 206. The edges from which the support arms 212 and 214 extend may be facing opposite to each other. The support arms 212 and 214 extend towards the second support portion 208 from the first support portion 210.

Each of the support arms may include interface surfaces. The support arm 212 may have an interface surface 220 and the support arm 214 may have an interface surface 222. The interface surfaces 220 and 222 of the support arms 212 and 214 of the first member 206 face away from the first support portion 210.

The support arms 212 and 214 may also include additional surfaces apart from the interface surfaces 220 and 222. Each one of the support arms 212 and 214 may include an anterior surface, a posterior surface, a surface that interfaces a surface of the first support portion 210, an external surface and an internal surface.

The external surface of the support arm 212 may be present on one side of the support arm 212 and the internal surface the support arm 212 may be present on the other side of the support arm 212, if viewed from the anterior direction. Similarly, the external surface of the support arm 214 may be present on one side of the support arm 214 and the internal surface the support arm 214 may be present on the other side of the support arm 214 if viewed from the anterior direction. The surface that interfaces a surface of the first support portion 210 may be facing away from the interface surfaces 220 and 222.

The first member 206 may further include a step 230. The step 230 may be provided on the interface surfaces 220 and 222. The step 230 may be configured such that it provides support to the support arms 212 and 214 from making movement sideward when the fusion cage 202 is in an expanded position.

The step 226 may assume a rectangular shape extending throughout the lengths of the support arms 212 and 214 and have a width extending in an inferior direction which may be facing away from the first support portion 210.

The external surface of the support arms 212 of the first member 206 may include slots 232. The slot 232 may be a trapezoidal aperture, when viewed from the anterior and the posterior sides with a depth cut towards the lateral direction of the support arm 212. The slots 232 may be configured to receive keys.

Similar slots 232 may be included on the internal surface of the support arm 214. Corresponding keys may be present on the support arms of the second member 208 which may be received by the slots 232.

The first member 206 may include a first channel 236. The first channel 236 may have a configuration such that it can accommodate the engagement member 204 either partially or entirely within the first channel 236.

The first channel 236 may be included on one of the surfaces of the support arm 212 of the first supporting portion 210 and may extend to an offset distance. The first channel 236 may be configured to receive the engagement member 204. The engagement member 204 may be partially or entirely received by the first channel 236.

The first channel 236 may be provided on the anterior surface of the support arm 212. The first channel 236 may have an orthogonal orientation with respect to the first support portion 210 of the first member 206.

The first channel 236 may further define a first neck member receiving portion 238, a first beam member receiving portion 240 and a beam connecting member receiving portion 242.

The first neck receiving portion 238 may receive at least a portion of a first neck member. The first beam member receiving portion 238 may receive a portion of a first beam member. The beam connecting member receiving portion 240 may receive a first portion of a beam connecting member.

Figure 2C:
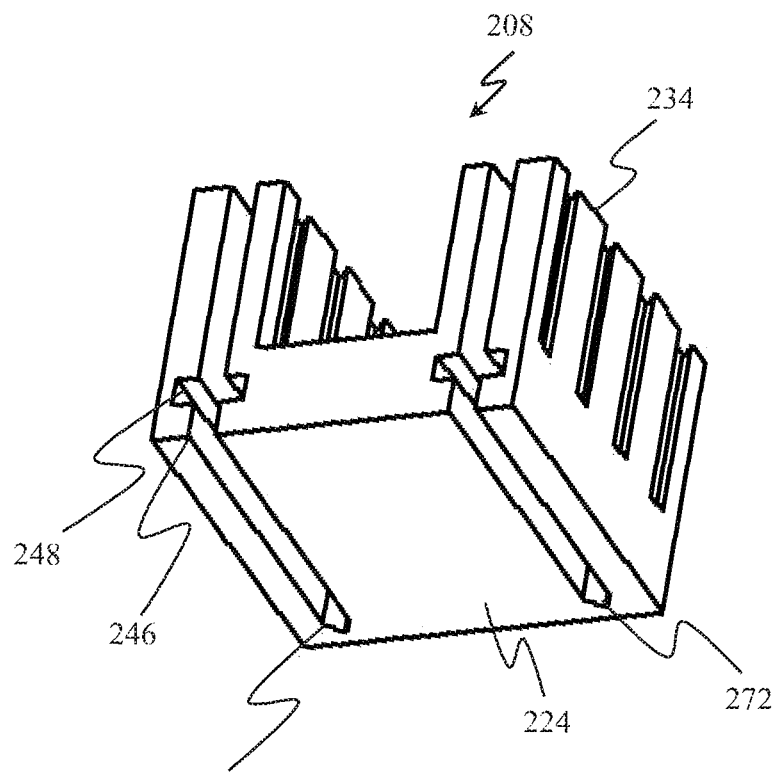
FIG. 2C is a bottom view of a second member of system 200.
Figure 2D:
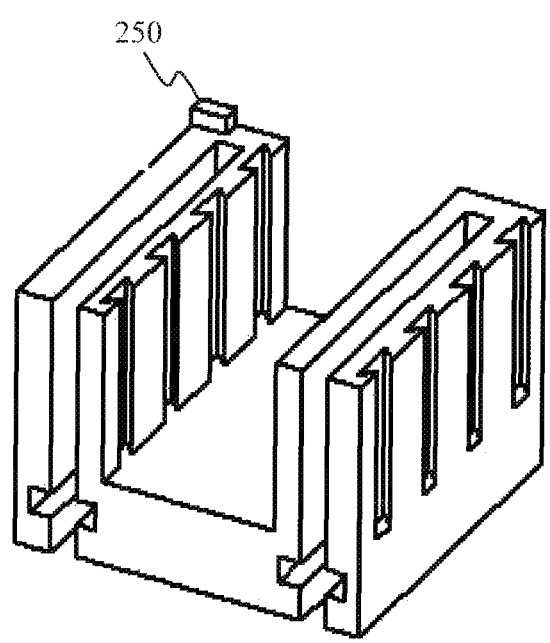
FIG. 2D is the top view of the second member of FIG. 2C.

Referring to FIGS. 2C-2D, the second member 208 may include a second support portion 224. The second support portion 224 of the second member 208 may interface with at least a surface of a second vertebral body.

The second member 208 may include a pair of support arms 216 and 218. The support arms 216 and 218 may extend from two edges of the first support portion 224 of the second member 208. The edges from which the support arm 216 and 218 extend may be facing opposite to each other. The support arms 216 and 218 extend towards the first support portion 210 from the second support portion 224.

Each of the support arms may include one or more interface surfaces. The support arm 216 may have an interface surface 226 and the support arm 218 may have an interface surface 228. The interface surfaces 226 and 228 of the support arms 216 and 218 of the second member 208 face away from the second support portion 224.

The support arms 216 and 218 may also include additional surfaces apart from the interface surfaces 226 and 228. Each one of the support arms 216 and 218 may include an anterior surface, a posterior surface, a surface that interfaces the second support portion 224, an external surface and an internal surface.

The external surface of the support arm 216 may be present on one side of the support arm 216 and the internal surface the support arm 216 may be present on the other side of the support arm 216, if viewed from the anterior direction. Similarly, the external surface of the support arm 218 may be present on one side of the support arm 218 and the internal surface the support arm 218 may be present on the other side of the support arm 218 if viewed from the anterior direction. The surface that interfaces a surface of the second support portion 224 may be facing away from the interface surfaces 226 and 228.

The second member 204 may further include a step 250 which may be similar in structure to the step 230. The step 250 may be provided on the interface surfaces 226 and 228. The step 250 may assume a rectangular shape extending throughout the lengths of the support arms 216 and 218 and have a width extending in a direction which may be facing away from the second support portion 224.

The step 230 may be configured such that the step 230 provides support to the support arms 216 and 218 from making a movement sideward when the fusion cage 202 is in an expanded position. The step 250 may be configured such that it provides support to the support arms 212 and 214 from making a movement sideward when the fusion cage 202 is in an expanded position.

The internal surface of the support arms 216 of the second member 208 may include keys 234. The key 234 may be a trapezoidal structure, when viewed from the anterior and the posterior sides with an extension towards the slot 232 in the lateral direction of the support arm 214. The keys 234 may be configured to be received by the slots 232. Similar keys 234 may be included on the external surface of the support arm 218.

The second member 208 may include a second channel 244. The second channel 244 may have a configuration such that it can accommodate the engagement member 204 either partially or entirely within the second channel 244.

The second channel 244 may be included on one of the surfaces of the support arm 216 of the second support portion 224 and may extend to an arbitrary distance in the anterior and posterior direction. The second channel 244 may be configured to receive the engagement member 204. The engagement member 204 may be partially or entirely received by the second channel 244.

The second channel 244 may be provided on the anterior surface of the support arm 216. The second channel 244 may include the second neck member receiving portion 246 and second beam member receiving portion 248. A portion of the beam connecting member receiving portion 242 may be included in the second channel 244. The second channel 244 may have an orthogonal orientation with respect to the second support portion 216 of the second member 208.

Figure 2E:
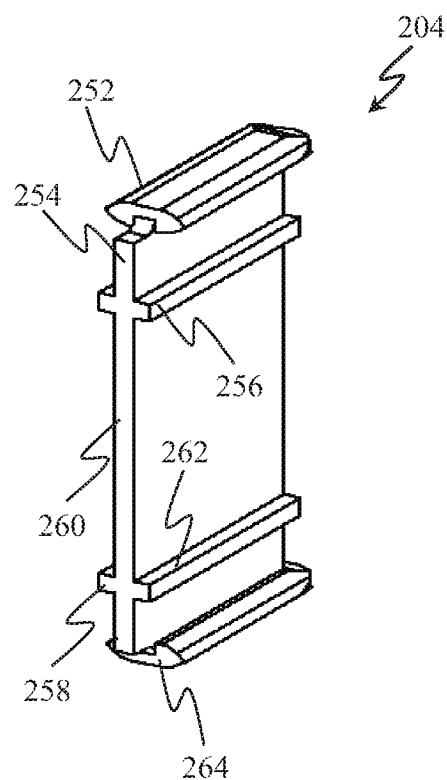
FIG. 2E is an isometric view of an engagement member of system 200.
Figure 2F:
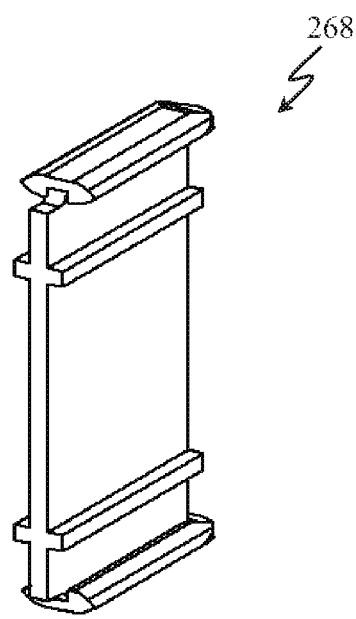
FIG. 2F is an isometric view of a second engagement member of system 200.

Referring to FIGS. 2E-2F, the engagement member 104 may comprise a first blade member 252, a first neck member 254, a first beam member 256, a second beam member 258 and a beam connecting member 260. The engagement member 204 may also be entirely received by the first channel 236 and the channel 244.

The first blade member 252 may be inserted into a first vertebral body. The first blade member 252 may have hexagonal structure if viewed from the anterior and posterior directions. The hexagonal first blade member 252 may have a width extended in the anterior posterior direction.

The first neck member 254 may provide a connection between the first blade member 252 and the first beam member 256. The first neck member 254 provides a support to the fusion cage 202 by connecting it with the first blade member 252. The first neck member 254 may have a rectangular body with a width extending from the anterior direction to the posterior direction.

The first beam member 256 may also assume a rectangular body with a width extending from the anterior direction to the posterior direction. The dimension of the first beam member 256 may be bigger than the first neck member 254.

The second beam member 258 may be positioned such that it is closer to the second vertebral body and farther from the first vertebral body. The beam connecting member 260 connects the first beam member 256 and the second beam member 258. The second beam member 258 may have a structure that resembles the first beam member 256.

The beam connecting member 260 may also have a rectangular body with a width extending in the anterior posterior direction. The dimension of the beam connecting member 260 may be similar to the first neck member 254.

The engagement member 254 may additionally have a second neck member 262 and a second blade member 264. The second neck member 262 may resemble the first neck member 254. The second blade member 264 may resemble the first blade member 252.

The second blade member 264 may be inserted into the second vertebral body. The second neck member 262 provides a connection between the second blade member 264 and the second beam member 258.

The first member 206 and the second member 208 may include a second engagement member 268, which resembles the engagement member 204. For the second engagement member 268 to be accommodated in the fusion cage 202, the first member 206 and the second member 208 may define addition channels 270 and 272.

Additional channel 270 may be a part of the first member 206 such that the additional channel 270 may be included on one of the surfaces of the support arm 214 of the first support portion 210 and may resemble the first channel 236.

Additional channel 272 may be a part of the second member 208 such that the additional channel 272 may be included on one of the surfaces of the support arm 218 of the second support portion 224 and may resemble the first channel 244.

Figure 2G:
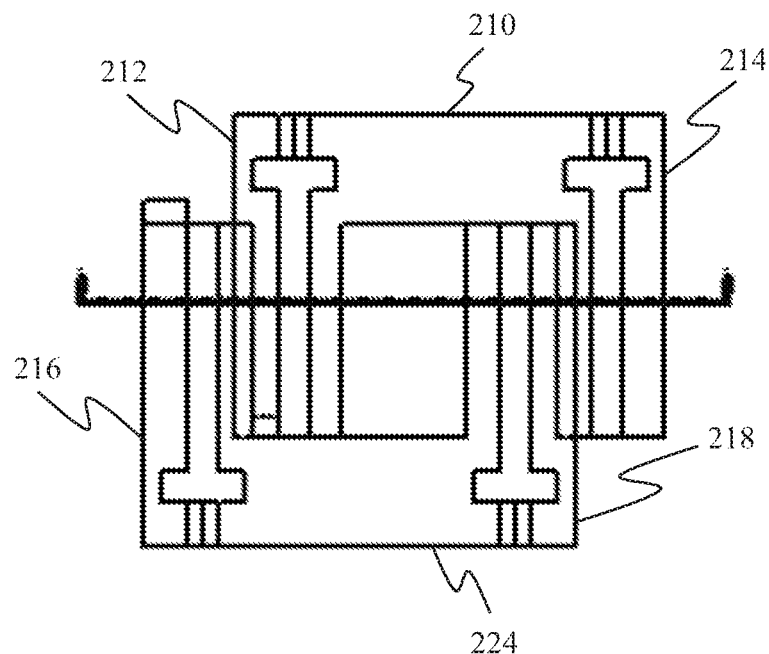
FIG. 2G is a front view of a collapsed position of system 200.
Figure 2H:
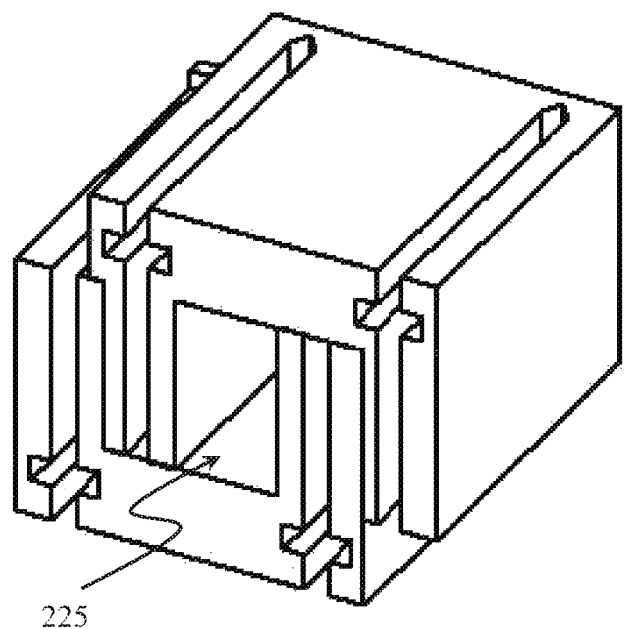
FIG. 2H is an isometric view of the collapsed position of FIG. 2G.

Referring to FIGS. 2G-2H, the support arms may be configured such that in a collapsed position, the support arms 212 and 214 extending from the first support portion 210 may be disposed into the second support portion 224 in a direction lateral to the support arms 216 and 218 extending from the second support portion 224. The configuration of the support arms 212 and 214 and the support arms 216 and 218, in a collapsed position may define a first space 225.

In the expanded position, a portion of one of the interface surfaces of each of the support arms of the first member 206 may interface with a portion of the interface surface of the support arms of the second member 208. For example, interface surface 220 of the support arm 212 interfaces with interface surface 226 of the support arm 216. Similarly, interface surface 222 of the support arm 214 interfaces with interface surface 228 of the support arm 218.

The slots 232 of the support arm 212 of the first member 206 may be received in the corresponding keys 234 of the support arm 216 of the second member 208 in a collapsed state. The reception of the keys 234 by the slots 232 ensure that, in the collapsed state, the movement of the first member 206 and the second member 208 may be prevented.

The first member 206 or the second member 208 may be pushed sideward such that the keys 234 engage into the slots 232. One of the first member 206 or the second member 208 may be pushed to an offset position in the superior inferior direction such that the grip between the key 234 and the slot 232 is tightened.

One of the first member 206 or the second member 208 may be pushed to an offset position in the superior inferior direction such that the grip between the key 234 and the slot 232 is loosened by the push. After the push, the first member 206 or the second member 208 may be moved sideward until the keys 234 are entirely disengaged from the slots 232. Once the keys 234 exit the slots 232, the first member 206 and the second member 208 become movable in a superior inferior direction.

The fusion cage 202 may be operated to assume the expanded position by moving one of the first member 206 or the second member 208 in a superior inferior direction. The movement in the superior inferior direction may occur along the longitudinal axis of the slots 232 and keys 234.

Figure 2I:
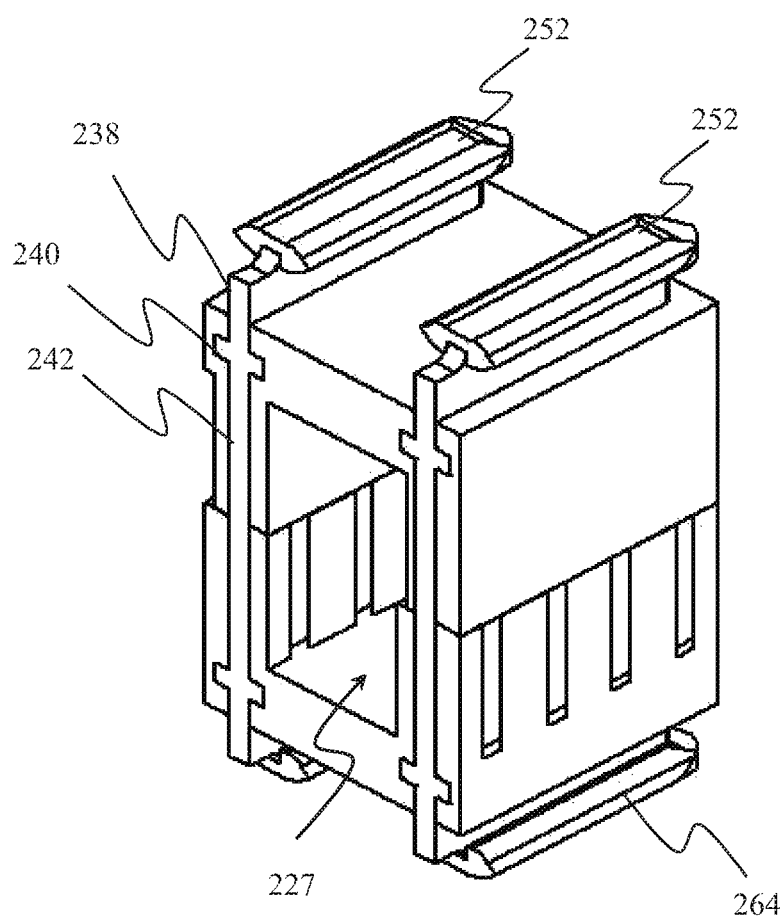
FIG. 2I is an isometric view of an expanded position of system 200.

Referring to FIG. 2I, while moving the first member 206 or the second member 208 in the superior inferior direction, the distance between the first support portion 210 and the second support portion 224 may increase thereby defining a second space 227 in the area between the first support portion 210, the second support portion 224 and the support arms 212, 214, 216 and 218. The empty space may be employed to accommodate the graft material during the fusion procedures.

Once the fusion cage 202 is expanded, one of the first member 206 or the second member 208 may be moved in a direction orthogonal to the longitudinal axis of the slots 232 and keys 234. By moving the first member 206 or the second member 208 in that direction it is ensured that further movement between the first member 206 and the second member 208 is prevented in the expanded position.

Upon moving one of the first member 206 or the second member 208 in a direction orthogonal to the longitudinal axis of the slots 232 and keys 234, an interface surface 220 coincides with another interface surface 226 and interface surface 222 coincides with another interface surface 228. Further, additional support is provided to the first member 206 and the second member 208 by employing steps 230 and steps 250.

In an expanded position, when one of the first member 206 or the second member 208 is moved along the longitudinal axis of the slots 232 and keys 234, the first channel 236 being a part of the first member 206 and the second channel 244 being a part of the second member 208, also move thereby making an alignment.

In an expanded position, the alignment of the first channel 236 with the second channel 244 makes way for the engagement member 104 to be disposed into the channels 236 and 244.

In an expanded position, the first neck member 254, the first beam member 256 and a part of the beam connecting member 260 may be inserted into the first channel 236. The second neck member 262, the second beam member 258 and a part of the beam connecting member 260 may be inserted into the second channel 244.

In an expanded position, the first neck member receiving portion 238 may receive the first neck member 254. The beam connecting member receiving portion 242 may receive the beam connecting member 260. The second beam member receiving portion 248 may receive the second beam member 258.

Referring to FIG. 3, a system 300 may include a fusion cage 302 and an engagement member 304. The fusion cage 302 may include a first member 306 and a second member 308.

The first member 306 may be an upper portion of the fusion cage 302 and the second member 308 may be a lower portion of the fusion cage 302. On the other hand, the first member 306 may be a lower portion of the fusion cage 302 and the second member 308 may be an upper portion of the fusion cage 302.

Figure 3A:
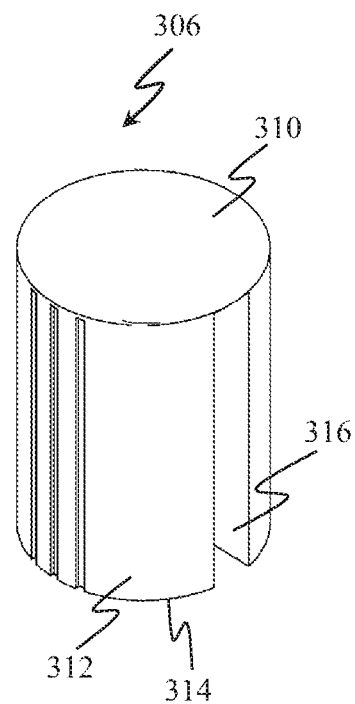
FIG. 3A is an isometric view of a first member of system 300.

Referring to FIG. 3A, the first member 306 may include a first support portion 310. The first support portion 310 of the first member 306 may interface with at least a surface of a first vertebral body.

The first member 306 may also include a support arm 312. The support arm 312 may extend from an edge of the first support portion 310 of the first member 306. The support arm 312 may extend towards a second support portion from the first support portion 310.

The support arm 312 may include a first interface surface 314. The first interface surface 314 may interface with at least a second interface surface of the second member 308. The first interface surface 314 may have a smaller footprint than the first support portion 310. The first interface surface 314 may be facing away from the first support portion 310.

A portion of the first member 306 may be folded in a collapsed position which can be expanded from within the second member 308.

A portion of the first member 306 may include a first channel 316 disposed at some portion between the first support portion 310 and the interface surface 314. The first channel 316 may be configured such that the first channel 316 accommodates a portion of the engagement member 304.

The first channel 316 may be configured such that a portion of it may be disposed within the first member 306. The first channel 316 may include a depth cut along its length towards the first interface surface 314 starting from a portion of the support arm 312. The dimension of the cut may bay be configured such that it accommodates a portion of the engagement member 304.

Figure 3B:
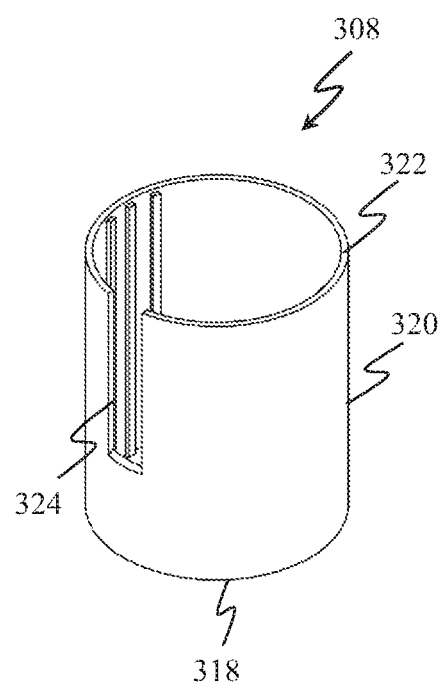
FIG. 3B is an isometric view of a second member of system 300.

Referring to FIG. 3B, the second member 308 may include a second support portion 318. The second support portion 318 of the second member 308 may interface with at least a surface of a first vertebral body.

The second member 308 may also include a support arm 320. The support arm 320 may extend from an edge of the second support portion 318 of the second member 308. The support arm 320 may extend towards the first support portion 310 from the second support portion 318.

The support arm 320 may include a second interface surface 322. The second interface surface 322 may interface with at least the first interface surface 314 of the first member 306. The second interface surface 322 may have a smaller footprint than the second support portion 318. The second interface surface 322 may be facing away from the second support portion 318.

A portion of the second member 308 may be folded in a collapsed position which may be expanded from within the first member 306.

A portion of the second member 308 may include a second channel 324 disposed at some portion between the second support portion 318 and the interface portion 320. The second channel 324 may be configured such that the second channel 324 accommodates a portion of the engagement member 304.

The second channel 324 may be configured such that a part of it may be disposed within the second member 308. The second channel 324 may include a depth cut along its length towards the second interface portion 320 starting from a portion of the connecting surface 322. The dimension of the cut may be configured such that it accommodates a portion of the engagement member 304.

Figure 3C:
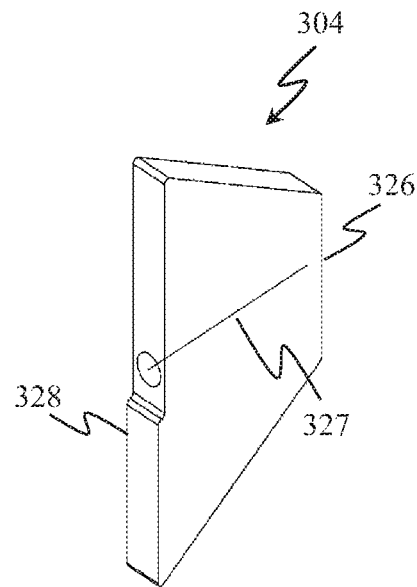
FIG. 3C is an isometric view of an engagement member.

Referring to FIG. 3C, the engagement member 304 may be a trapezoidal shaped member from one perspective creating a thin tapered insert with a first surface 326 and a second surface 328. The first surface 326 of the engagement member 304 may be smaller than the second surface 328. The first surface 326 may be inserted first into the channels 316 and 324. The second surface 328 follows the first surface 325 into the channels 316 and 324.

The engagement member 304 may include an additional channel 330. The additional channel 330 may extend within its body from the second surface 328 towards the first surface 326 along an axis 327. The axis 327 may extend from the second surface 328 to the first surface 326 in the lateral direction of the engagement member 304. The additional channel 330 may have internal threads partially or entirely throughout the length of the additional channel 330.

Figure 3D:
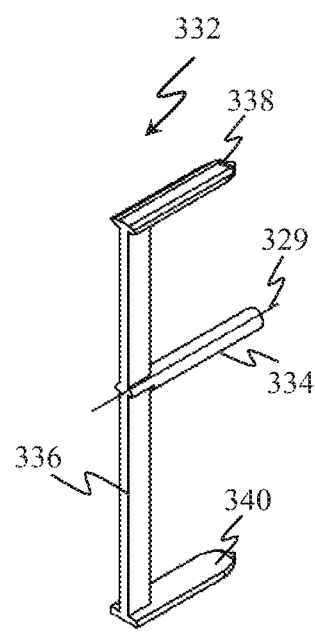
FIG. 3D is an isometric view of a second engagement member.

Referring to FIG. 3D, the system 300 may include a second engagement member 332. The second engagement member 332 may include a blade 334 which may be inserted into the additional channel 330. The blade 334 may assume a length in the lateral direction.

The blade 334 may extend externally from a blade anchor 336 along an axis 329. The axis 329 may extend from the blade anchor 336 in the lateral direction. The blade 334 may have an orthogonal orientation with respect to the blade anchor 336 from which the blade 334 extends.

The blade anchor 336 may assume a length in the superior interior direction. The blade 334 may be disposed at the midpoint of the blade anchor 336. The blade anchor 336 may include additional blades disposed at the proximal end and the distal end of the blade anchor 336.

The blade 334 may be configured such that a portion of it may be inserted into at least a portion of the additional channel 330.

A blade 338 may resemble the blade 334 and may extend in the lateral direction at the proximal end of the blade anchor 336. The blade 338 may be configured such that a portion of it may be inserted into at least a portion of the first vertebral body.

A blade 340 may resemble the blade 334 and may extend in the lateral direction at the distal end of the blade anchor 336. The blade 340 may be configured such that a portion of it may be inserted into the second vertebral body.

The blades 334, 338 and 340 and the blade anchor 336 may form an E shaped structure from the anterior direction. The blade 334 may be positioned relatively half way between the blade 338 and blade 340.

Figure 3E:
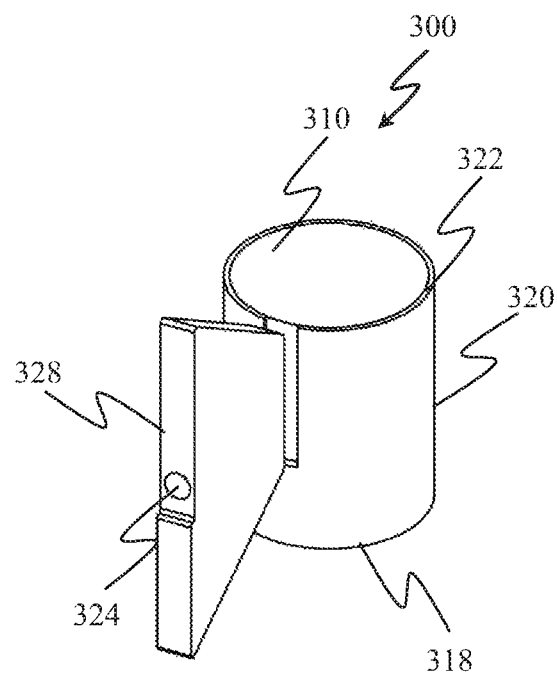
FIG. 3E is an isometric view of a collapsed position of system 300.

Referring to FIG. 3E, in the collapsed position, a portion of the first member 306 or the second member 308 may be folded within the other member and may be expanded from within the other member.

Figure 3F:
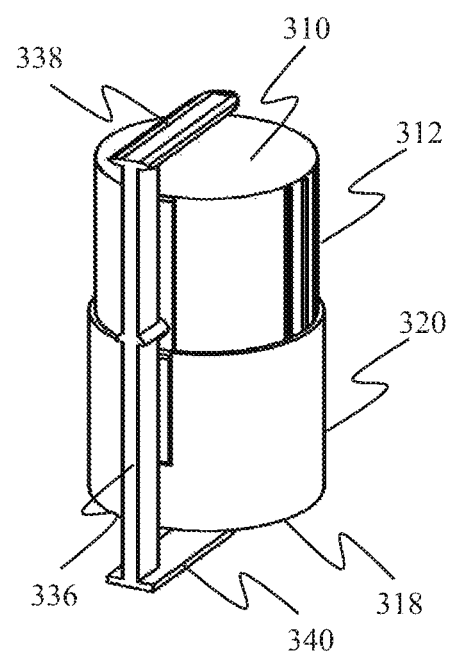
FIG. 3F is an isometric view of an expanded position of system 300.

Referring to FIG. 3F, in the expanded position, the first channel 316 and the second channel 324 may define a trapezoidal aperture 325 with a depth which may accommodate the engagement member 304.

The first surface 326 of the engagement member 304 may be inserted first into the trapezoidal aperture 325. The second surface 328 follows the first surface 325 into the trapezoidal aperture 325. The engagement member 304 may be received by the trapezoidal aperture 325. The engagement member 304 may ensure prevention to the first member 306 and the second member 308 in the expanded position from backing out of the expanded position.

The second engagement member 332 may provide additional support to the fusion cage 302 to maintain the expanded position. The blade 334 of the second engagement member 332 may be inserted into the additional channel 330 of the engagement member 304. The blades 338 may be inserted into the first vertebral body and the blade 340 may be inserted into the second vertebral body.

The insertion of the blade 338 into the first vertebral body and the insertion of the blade 340 into the second vertebral body may ensure a secure fastening of the fusion cage 302 in between the first vertebral body and the second vertebral body in an expanded position.

Referring to FIG. 4, a system 400 may be used for providing support to two adjacent vertebral bodies. The system 400 may include a fusion cage 402 and an engagement member 404.

Figure 4A:
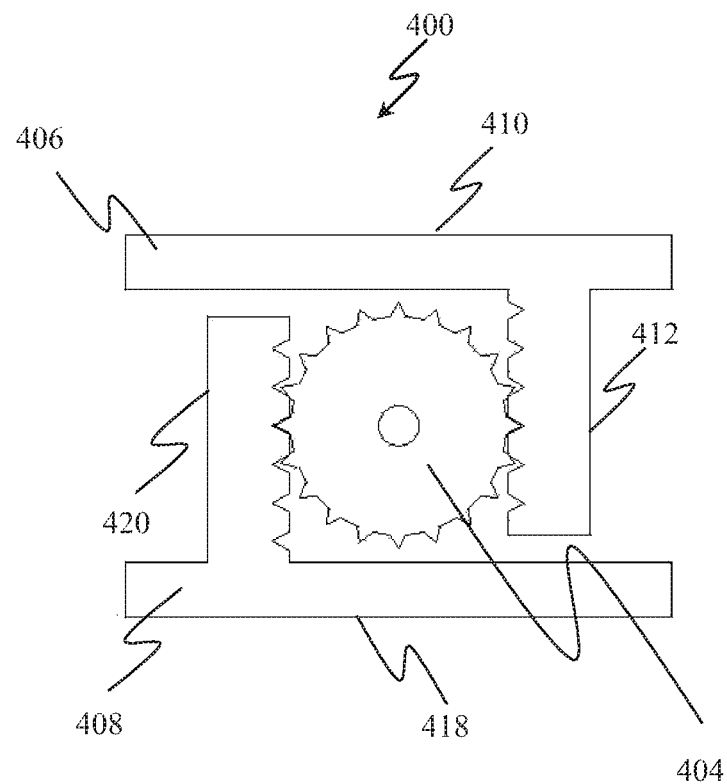
FIG. 4A is a front view of a collapsed position of system 400.
Figure 4B:
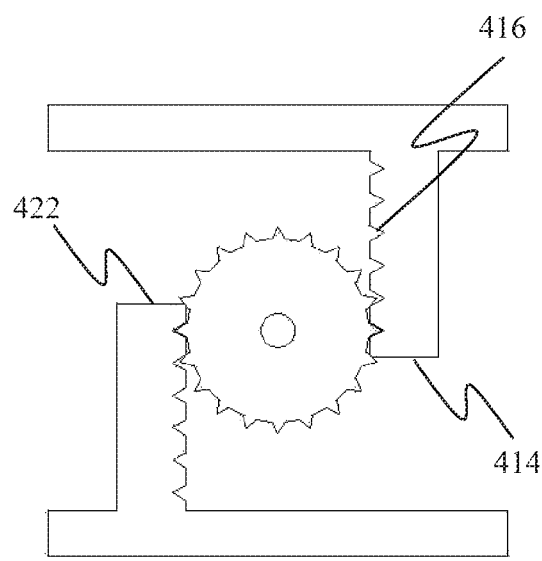
FIG. 4B is a front view of an expanded position of system 400.

Referring to FIGS. 4A-4B, the fusion cage 402 includes a first member 406 and a second member 408.

The first member 406 may include a first support portion 410. The first support portion 410 of the first member 406 may interface with at least a surface of the first vertebral body.

The first member 406 may include a support arm 412. The support arm 412 and may extend an edge of the first support portion 410 of the first member 406. The support arm 412 may extend towards a second support portion from the first support portion 410.

The support arm 412 may include an interface surface 414. The interface surface 414 may be facing away from the first support portion 410. The interface surface may interface at least a surface of the second member 408.

The support arm 412 may also include an anterior surface, a posterior surface, an external surface, an internal surface and a surface that joins the first support portion 410. The internal surface of the support arm 412 may include slots 416. The slots 416 may assume triangular toothed structure. The internal surface of the support arm 412 may interface at least a portion of the engagement member 404.

The second member 408 may include a second support portion 418. The first second support portion 418 of the second member 408 may interface with at least a surface of the second vertebral body.

The second member 408 may include a support arm 420. The support arm 420 and may extend from an edge of the second support portion 418 of the second member 408. The support arm 420 may extend towards the first support portion 410 from the second support portion 418.

The support arm 420 may include an interface surface 422. The interface surface 422 may be facing away from the second support portion 418. The interface surface 422 may interface at least a surface of the first member 406.

The support arm 420 may also include an anterior surface, a posterior surface, an external surface, an internal surface and a surface that joins the second support portion 418. The internal surface of the support arm 420 may include slots 424. The slots 424 may assume triangular toothed structure. The internal surface of the support arm 420 may interface at least a portion of the engagement member 404.

The engagement member 404 may be a rotational gear positioned between the first support portion 410 and the second support portion 418.

The slots 416 and slots 424 may be facing the rotational gear 404. The slots 416 and slots 424 provide a ratcheting mechanism to engage the rotational gear 404. As the rotational gear 404 is rotated the first support portion 410 and the second support portion 418 may extend away from each other.

In the expanded position, the first support portion 410 interfaces at least a surface of the first vertebral body and the second support portion 418 interfaces at least a surface of the second vertebral body.

Figure 5A:
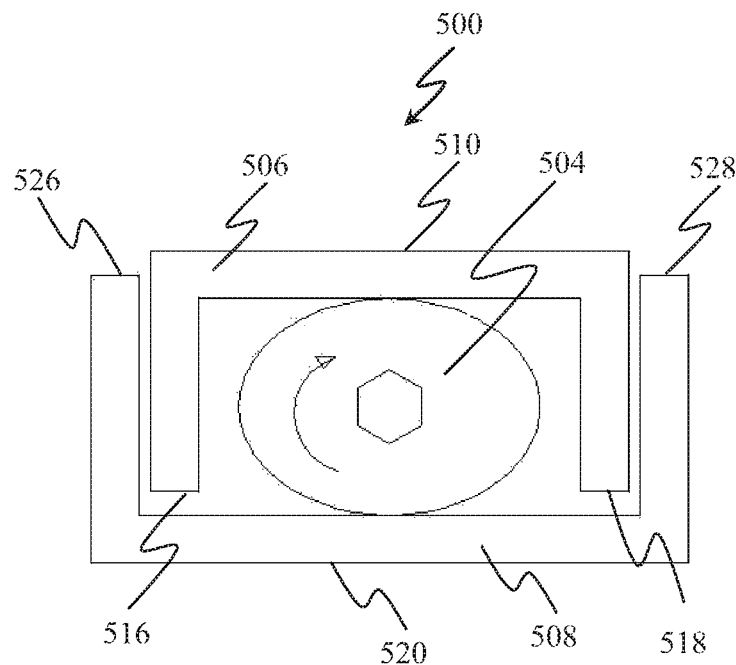
FIG. 5A is a front view of a collapsed position of system 500.
Figure 5B:
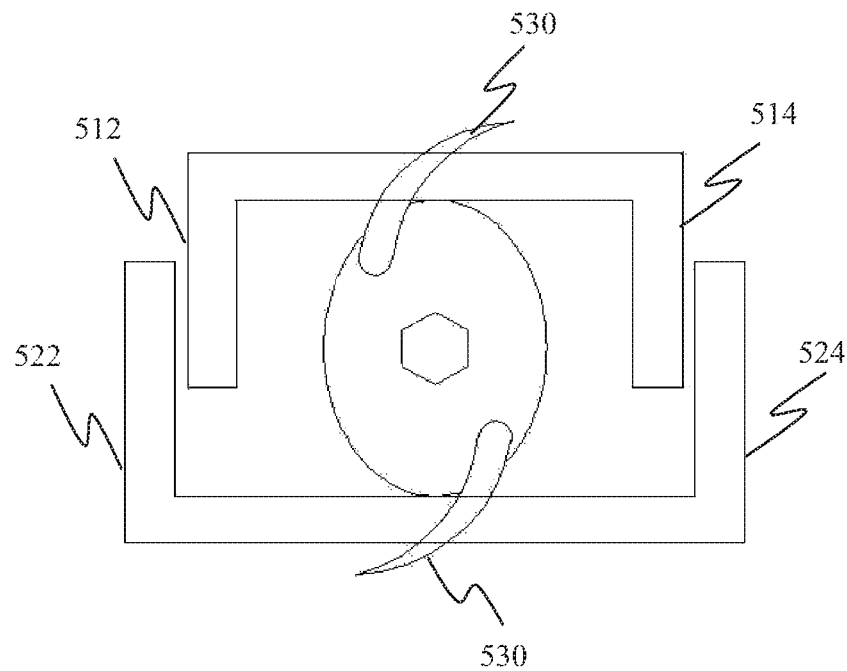
FIG. 5B is a front view of an expanded position of system 500.

Referring to FIGS. 5A-5B, a system 500 may be used for providing support to two adjacent vertebral bodies. The system 500 may include a fusion cage 502 and an engagement member 504. The fusion cage 502 includes a first member 506 and a second member 508.

The first member 506 may include a first support portion 510. The first support portion 510 of the first member 506 may interface with at least a surface of the first vertebral body.

The first member 506 may include a pair support arms 512 and 514. The support arms 512 and 514 may extend from two edges of the first support portion 510 of the first member 506. The support arms 512 and 514 may extend towards a second support portion from the first support portion 510.

Each of the support arms may include interface surfaces. The support arm 512 may have an interface surface 516 and the support arm 514 may have an interface surface 518. The interface surfaces 516 and 518 of the support arms 512 and 514 of the first member 506 face away from the first support portion 510.

The second member 508 may include a second support portion 520. The second support portion 520 of the second member 508 may interface with at least a surface of the first vertebral body.

The second member 508 may include a pair support arms 522 and 524. The support arms 522 and 524 may extend from two edges of the second support portion 520 of the second member 508. The support arms 522 and 524 may extend towards the first support portion 510 from the second support portion 520.

Each of the support arms may include interface surfaces. The support arm 522 may have an interface surface 526 and the support arm 524 may have an interface surface 528. The interface surfaces 526 and 528 of the support arms 522 and 524 of the second member 508 face away from the second support portion 520.

The engagement member 504 may be an oblong shaped cam. The engagement member 504 may be disposed between the first member 506 and the second member 504. A portion of the engagement member 504 at the proximal end interfaces a surface of the first support portion 510. A portion of the engagement member 504 at the distal end interfaces a surface of the second support portion 520.

In the collapsed state, the oblong cam 504 may assume a shape such that the diameter of the oblong cam 504 may be extended more along the lateral direction on both sides. Hence the oblong cam 504 may be wider than it is tall in the collapsed position.

A portion of the first member 506 may partially reside within the second member 508, in the collapsed position.

The oblong cam 504 may be actuated such that the oblong cam 504 may assume a different shape. The oblong cam 504, upon actuation, may assume a shape such that the diameter of the oblong cam 504 may be extended more along the superior inferior direction. Hence, in its expanded state the oblong cam 504 may be taller than it is wide.

The shape of the oblong cam 504 may extend the space between the first support portion 510 and the second support portion 520 thereby expanding the distance between the first member 506 and the second member 508.

The system 500 may include a second engagement member 530. The second engagement member 530 may be one or more retractable blades.

The retractable blades 530 may be employed to prevent the oblong cam 504 and the fusion cage 502 from sliding back to the collapsed position. The blades 530 may be retracted when the oblong cam 504 is in its collapsed state. The blades 530 may be deployed with the same instrument used to actuate the cam 504 and are deployed when the cam 504 is in the expanded position.

Figure 6A:
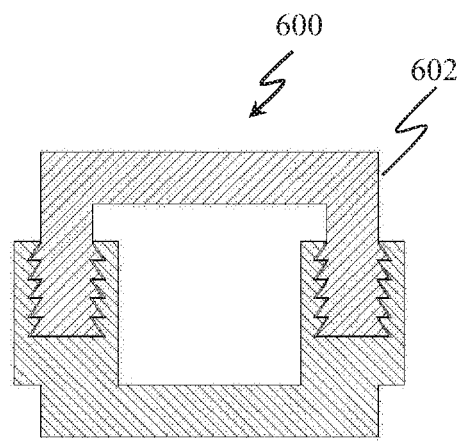
FIG. 6A is a collapsed cross section view of system 600.
Figure 6B:
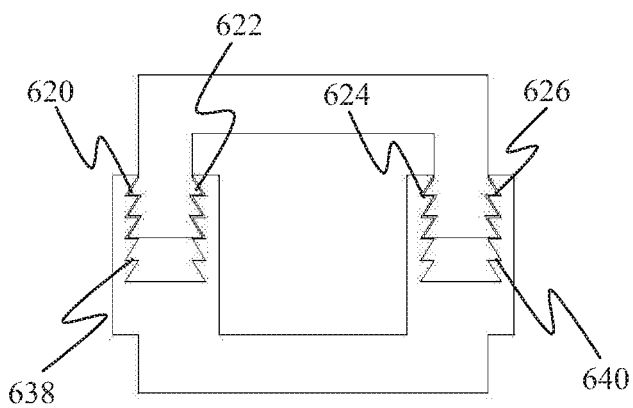
FIG. 6B is an expanded view of system 600.
Figure 6C:
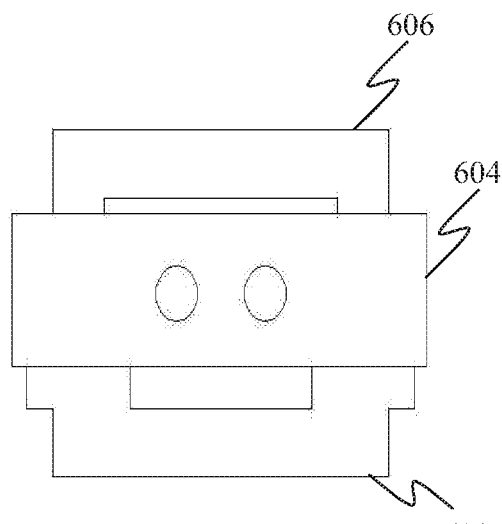
FIG. 6C is an expanded view with an engagement member of system 600.

Referring to FIGS. 6A-6C, a system 600 may be used for providing support to two adjacent vertebral bodies. The system 600 may include a fusion cage 602 and an engagement member 604. The fusion cage 602 includes a first member 606 and a second member 608.

The first member 606 may include a first support portion. The first support portion of the first member 606 may interface with at least a surface of the first vertebral body.

The first member 606 may include a pair support arm. The support arms may extend from two edges of the first support portion of the first member 606. The support arms may extend towards a second support portion from the first support portion.

The internal surface and the external surface of the support arm 612 may include keys 620 and 622. Similarly, the internal surface and the external surface of the support arm 614 may include keys 624 and 626. The keys 620, 622, 624 and 626 may include toothed structures. The keys 620, 622, 624 and 626 may be received by corresponding slots provided in the support arms of the second member 608.

The second member 608 may include a second support portion. The second support portion of the second member 608 may interface with at least a surface of the first vertebral body.

The second member 608 may include a pair support arms. The support arms may extend from two edges of the second support portion of the second member 608. The support arms may extend towards the first support portion 610 from the second support portion 624.

The second member 608 may include slots 638 and 640. The slots 638 and 640 may assume toothed structures. The slots 638 and 640 may be present two opposite surface of each of the rectangular apertures. The slots 638 may receive the keys 620 and 622 and slots 640 may receive the keys 624 and 626.

The keys 620, 622, 624 and 626 are fastened within the slots 638 and 640 by means of a ratchet system.

The engagement member 604 may be a locking plate. A second engagement member may be used in conjunction with the engagement member 604. The second engagement member may include one or more pins. The locking plate 604 may extend in an anterior posterior direction. The pins with the plate 604 engage the fusion cage 602 and lock the fusion cage 602 in an expanded position.

Figure 7:
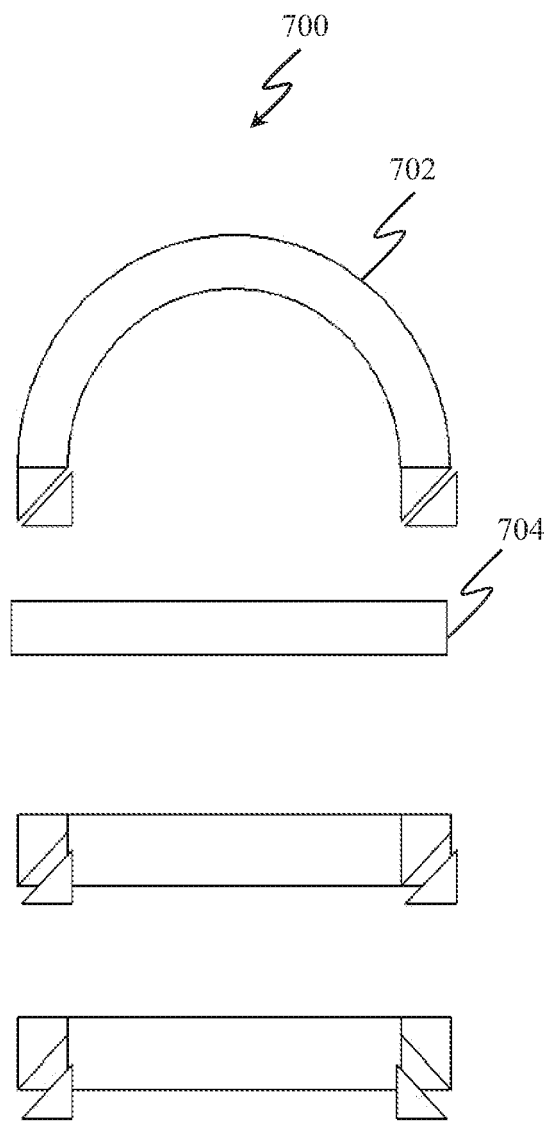
FIG. 7 is a superior view of system 700.

Referring to FIG. 7, a system 700 may include a fusion cage 702 and an engagement member 704. The fusion cage 702 may be shaped like a horse-shoe or assume a U-shape from the superior direction. At least one surface of each of the two support arms of the U shape may include an engagement member 704 which may be movable in such a manner to expand the fusion cage 702 in a superior-inferior direction. The second engagement member 704 may move in the same direction or opposite directions depending on the configuration. The system 700 may also include a support arm which extends from one arm of the fusion cage 702 to the other arm of the fusion cage 702 in the lateral direction.

Figure 8:
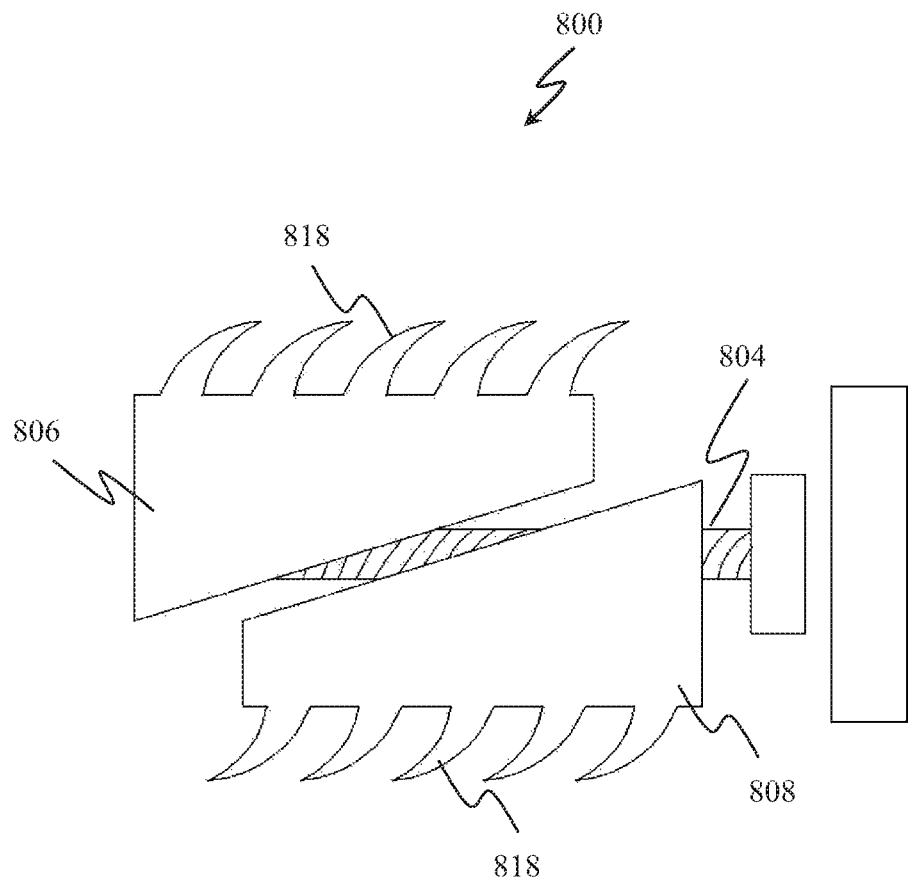
FIG. 8 is a front view of a system 800.

Referring to FIG. 8, a system 800 may include a fusion cage 802 and an engagement member 804. The fusion cage 802 may include a first member 806 and a second member 808.

The first member 806 may include a first support portion 810. A surface of the first support portion 810 may interface with at least a surface of the first vertebral body.

The first member 806 may include a first channel to receive the engagement member 804 in an expanded position. The first channel may include threads partially or entirely throughout its length.

The second member 808 may include a second support portion. A surface of the second support portion may interface with at least a surface of the first vertebral body.

The second member 808 may include a second channel to allow for passage of the engagement member 804. The second channel 816 may include threads partially or entirely throughout its length.

The engagement member 804 may be inserted through the second channel and extends to the first channel causing the first member 806 to expand in a superior inferior direction.

From a superior view the fusion cage 802 may be U-shaped with engagement members 804 on both arms of the U-shaped body. A second engagement member may be positioned to cover the opening of the U-shaped body.

The second engagement member 818 may be employed to capture the engagement members 804 and lock them in place in the expanded position. The second engagement member 818 may include openings which may allow for packing of graft material within the U-shaped body of the cage 802.

A surface of the first support portion and a surface of the second support portion may include serrations or teeth. The serrations on surface of the first support portion may be employed to engage the first member 806 with a surface of the first vertebral body. The serrations on surface of the second support portion may be employed to engage the second member 808 with a surface of the second vertebral body.

Figure 9:
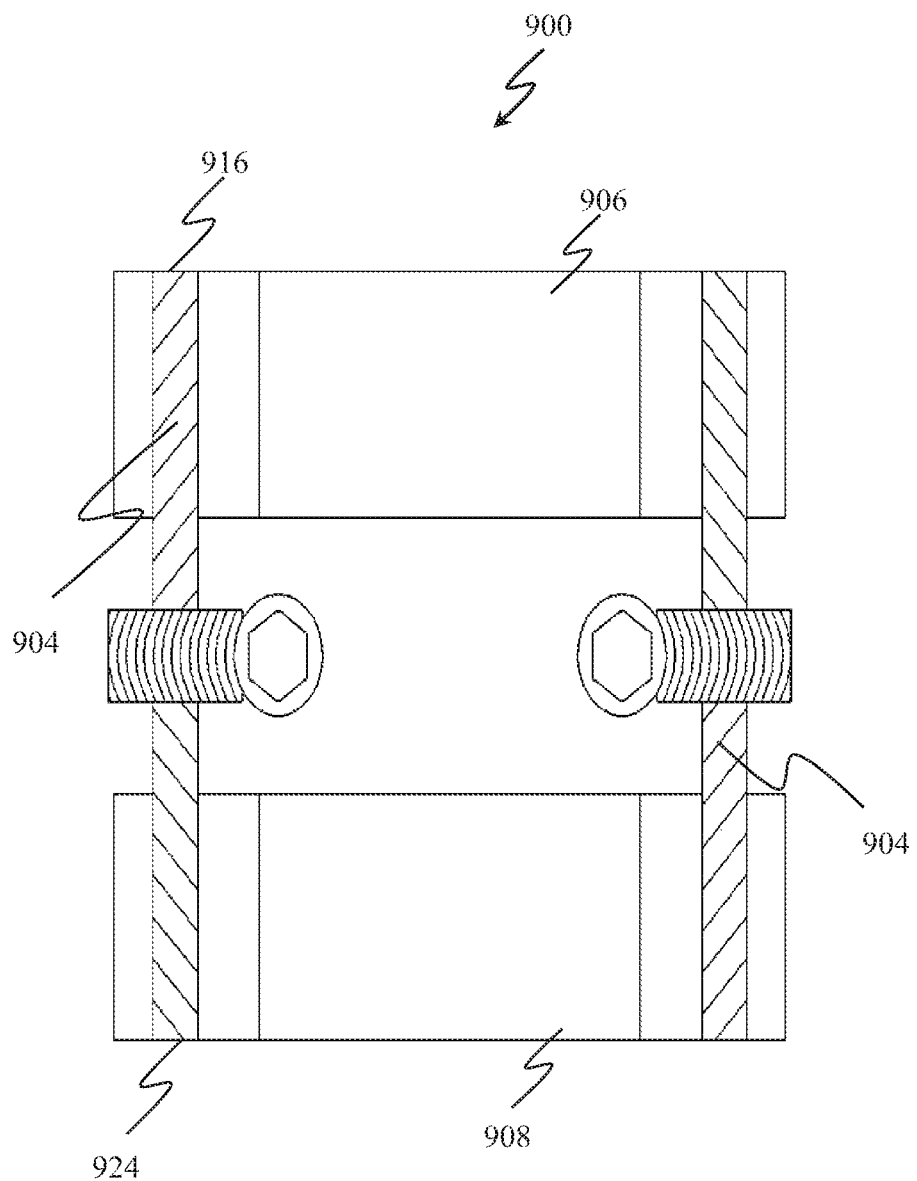
FIG. 9 is a front view of system 900.

Referring to FIG. 9, a system 900 may include a fusion cage 902 and an engagement member 904. The fusion cage 902 includes a first member 906 and a second member 908.

The first member 906 may assume a U-shaped rectangular body from a superior view. The first member 906 may include channel 916 for receiving the engagement member 904. There may be one or many channels 916 for receiving the engagement members 904. The channels 916 are positioned at the corners of the rectangular body. The channel 916 may be partially or fully threaded throughout its length.

The second member 908 may assume a U-shaped rectangular body from a superior view. The second member 908 may include channel 924 for receiving the engagement member 904. There may be one or many channels 924 for receiving the engagement members 904. The channels 924 are positioned at the corners of the rectangular body. The channel 924 may be partially or fully threaded throughout its length.

The engagement member 904 may be a screw which may be turned causing the first member 906 and the second member 908 to extend away from one another in a superior inferior direction.

The engagement member 904 may include a middle portion 926 for rotation of the engagement member 904. The engagement member 904 may include threads on its body on either side of the middle portion.

The engagement member 904 may allow expansion and retraction of the cage 902. A second engagement member 926 may be employed to close off the open end of the rectangular body and to maintain an expanded position of the fusion cage 902.

Figure 10:
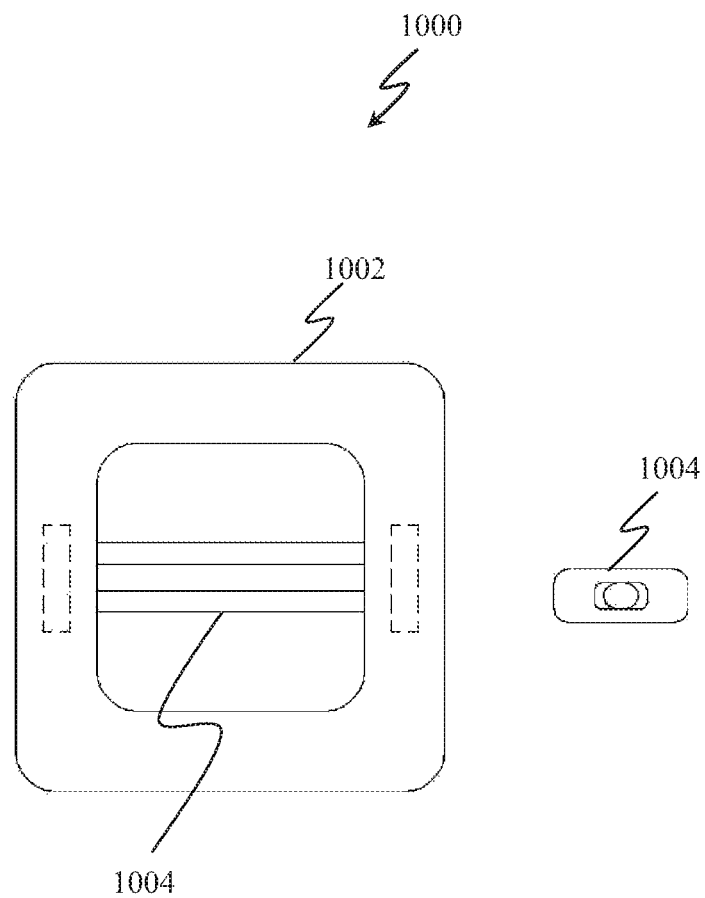
FIG. 10 is a superior view of system 1000.

Referring to FIG. 10, a system 1000 may include a fusion cage 1002 and an engagement member 1004. The cage 1010 may assume a closed body with a central opening from a superior view. More than one engagement member 1004 may be present in the system 1000. The engagement member(s) 1004 may be coaxial and may extend anterior to posterior through the central opening engaging opposite sides of the cage 1002. The engagement member(s) 1004 may adjust the fusion cage 1002 to provide lordosis adjustment.

An anterior view of the cage 1002 shows that the engagement member(s) 1004 may be rotated by rotating a part of them which extends from the engagement member(s) 1004. This part of an engagement member 1004 may include a drive socket and may be rotated to adjust the height of the cage 1002.

Figure 11:
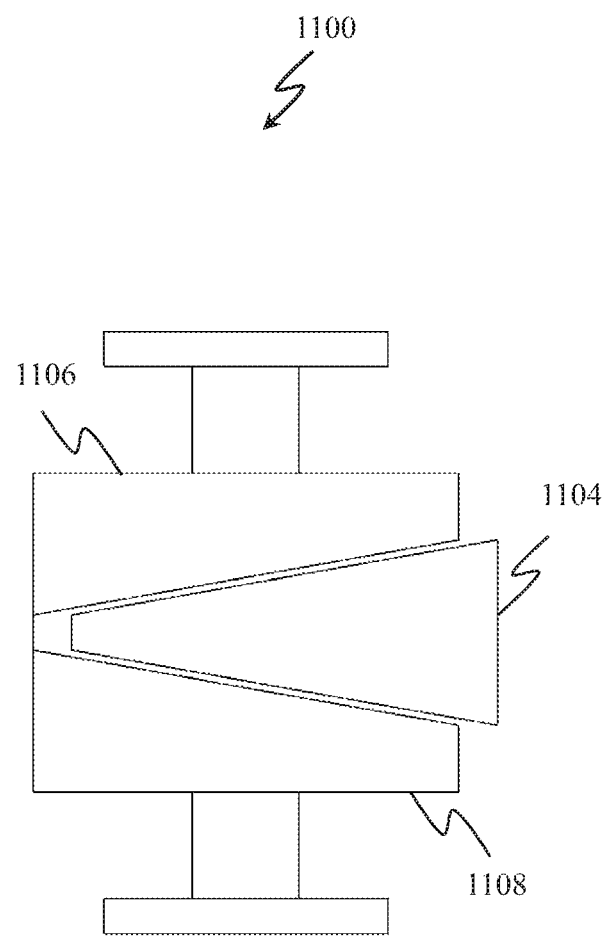
FIG. 11 is a front view of the system 1000 of FIG. 10.

Referring to FIG. 11, a system 1100 may include a fusion cage 1102 and an engagement member 1104. The fusion cage 1102 may include a first member 1106 and a second member 1108.

The engagement member 1104 may be inserted in a medial lateral direction between the first member 1106 and the second member 1108. The engagement member 1104 may be used to expand the cage 1102 by engaging between the first member 1106 and the second member 1108.

The engagement member 1104 may also include wings, barbs, ridges or the like to prevent withdrawal of the engagement member 1104 from between the first member 1106 and the second member 1108. Second engagement members may be used to fix first member 1106 and the second member 1108 to the adjacent vertebral bodies.

Figure 12A:
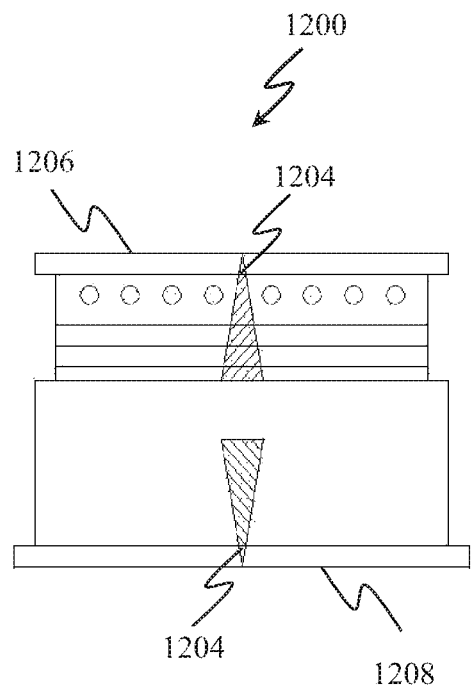
FIG. 12A is a front view of a collapsed position of system 1200.
Figure 12B:
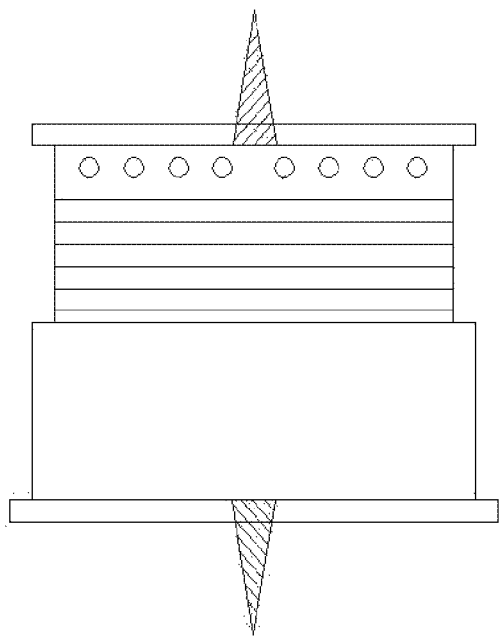
FIG. 12B is a front view of an expanded position of system 1200.

Referring to FIGS. 12A-12B, a system 1200 may include a fusion cage 1202 and an engagement member 1204. The fusion cage 1202 may include a first member 1206 and a second member 1208.

The first member 1206 may include a first support portion. The first support portion may include a channel. The channel may extend in a superior inferior direction along the first support portion. The channel may include threads along its length either partially or entirely.

The second member 1208 may include a second support portion. The second support portion may include a channel. The channel may extend in a superior inferior direction along the second support portion. The channel may include threads along its length either partially or entirely.

The channels may be aligned in a collapsed position as well as in an expanded position. The first member 1206 and the second member 1208 may be engaged via the threaded channels.

When the threaded channels are actuated, the first member 1206 and the second member 1208 expand in a superior-inferior direction.

The first member 1206 may include an additional channel. The additional channel accommodates a second engagement member. The second engagement member may be a spanner wrench. The spanner wrench may allow the cage 1202 to be expanded.

The engagement member 1204 may also include features such as retracted spikes or bone engagement features which may be actuated after expansion of the cage. The spikes or bone engagement features engage the adjacent bone. The spikes or bone engagement features may be threaded.

Figure 13:
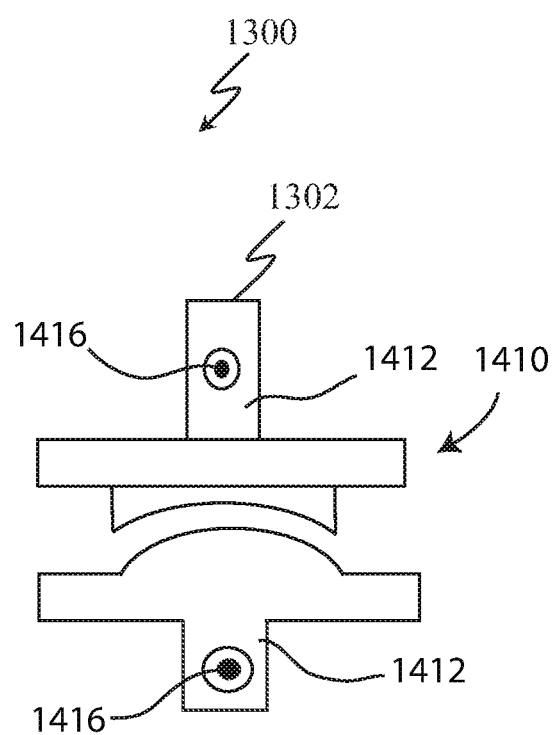
FIG. 13 is an anterior view of system 1300.

Referring to FIG. 13, a system 1300 may be used for providing support to two adjacent vertebral bodies. The system 1300 may include a fusion cage 1302 and an engagement member 1304. The system 1300 may incorporate an anterior posterior fusion cage 1302. The fusion cage 1302 may be a keel.

The fusion cage 1302 may be actuated with the engagement member 1304. Once the fusion cage 1302 is implanted, the engagement member 1304 may be actuated.

The system 1300 may include a second engagement member 1306 which may be provided on the sides of the fusion cage 1302.

The actuation of the fusion cage 1302 by the engagement member 1304 causes the second engagement member 1306 provided on the sides of the fusion cage 1302 to rotate outward into the bone space. The second engagement member 1306 increases the fixation within the bone and resists direction of the expulsion forces.

The engagement member 1304 may be a cam that has the barb-like feature contained within the cage 1302 in one position, and protruding from the cage 1302 when rotated 90 degrees.

Once the fusion cage 1302 is placed between two vertebral bodies, the second engagement member 1306 may be deployed into the vertebral body to resist pull-out of expulsion and help support or augment the engagement.

The fusion cage 1302 may be actuated via a screw mechanism, cam wedge/taper, or other means. The second engagement member 1306 may be composed of material that is flexible or slotted to be flexible, so that once deformed portions are deployed into the bone. The second engagement member 1306 may be a helical blade that may be captured upon insertion, but once rotated it may protrude out of the cage 1302 into the bone.

Figure 14A:
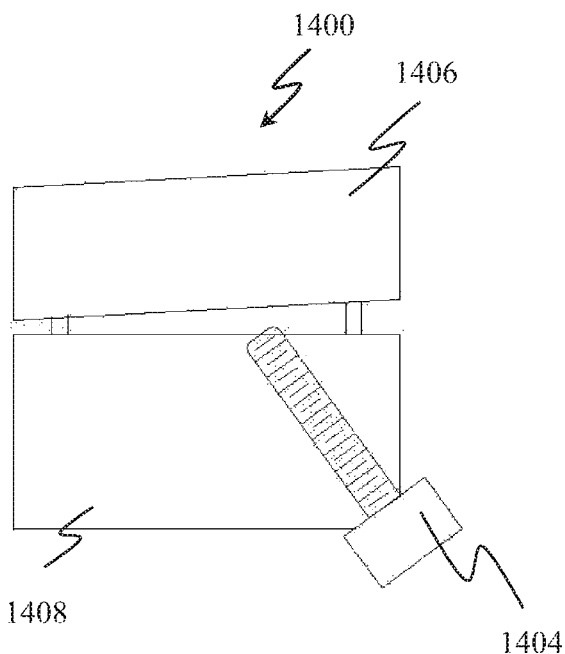
FIG. 14A is a front view of a collapsed position of system 1400.
Figure 14B:
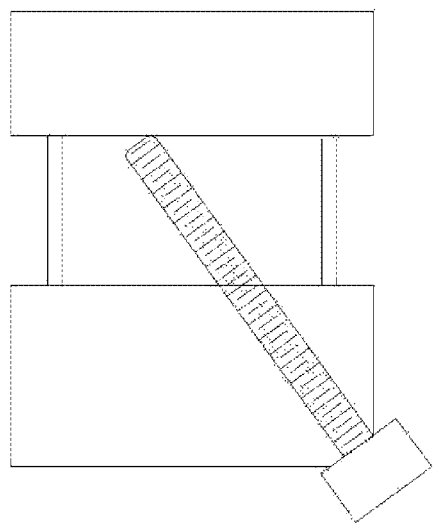
FIG. 14B is front view of an expanded position of system 1400.

Referring to FIG. 14, a system 1400 may be used for providing support to two adjacent vertebral bodies. The system 1400 may include a fusion cage 1402 and an engagement member 1404.

The fusion cage 1402 may include a first member 1406 and a second member 1408.

The first member 1406 may include a support arm which may be a linear slide placed at a plethora of positions between the first member 1406 and the second member 1408. The support arm 1412 may be extending towards the second member 1408 from the first member 1406

The first member 1406 may include a first channel to receive the engagement member 1404. The first channel may be partially or fully threaded along its length. The first channel may have an oblique orientation with respect to the first support portion.

The second member 1408 may include a second support portion which may be a linear slide placed at a plethora of positions between the first member 1406 and the second member 1408.

The second member 1408 may include a second channel to receive the engagement member 1404. The second channel may be partially or fully threaded along its length. The second channel may have an oblique orientation with respect to the second support portion.

The engagement member 1404 may be a jacking screw. The engagement member 1404 may be partially or fully threaded along its length. The engagement member 1404 may extend from the second channel to the first channel.

The engagement member 1404 may be actuated with a rotation nut toward the second support portion.

The engagement member 1404 may engage the first member 1406 extending the support arm and increasing the space between the first member 1406 and bottom second member 1408 to an expanded position.

Figure 15:
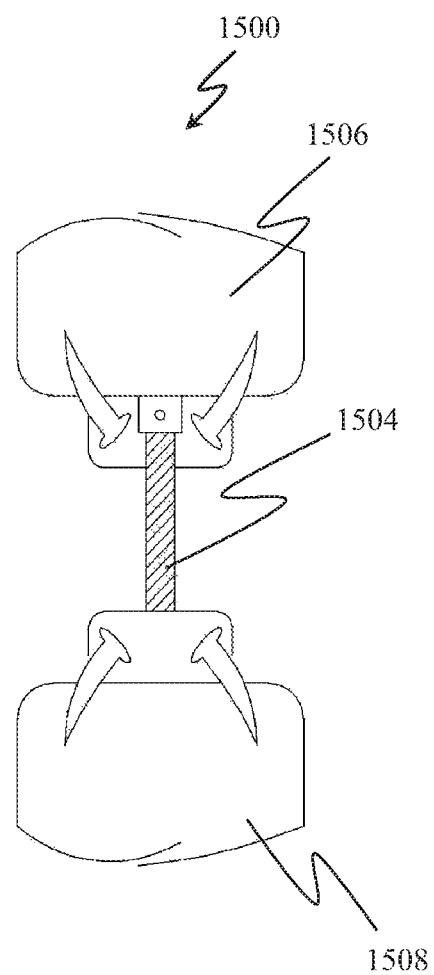
FIG. 15 is a front view of system 1500.

Referring to FIG. 15, a system a system 1500 may be used for providing support to two adjacent vertebral bodies. The system 1500 may include a fusion cage 1502 and an engagement member 1504. The fusion cage 1502 may include a first member 1506 and a second member 1508.

The first member 1506 may include provisions for holding second engagement members for engaging the first support portion with the first vertebral body. The first member 1506 may include more than one second engagement member.

The second member 1508 may include a second support portion. The second support portion may interface a surface of the second vertebral body.

The second member 1508 may include provisions for holding second engagement members for engaging the first support portion with the first vertebral body. The first member 1506 may include more than one second engagement members.

The engagement member 1504 may be disposed in between the first member 1506 and the second member 1508.

The more than one second engagement members may be provided at obtuse angles with respect to the first support portion to engage with the adjacent vertebral bodies.

Multiple drive features may be employed as described in the previous embodiments to drive the engagement member 1504 to expand the space between the first member 1506 and the second member 1508.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to fusion cages. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for supporting a first vertebral body and a second vertebral body, comprising:
   an expandable member configured to move between a collapsed position and an expanded position, the expandable member including:
      a first member including a first support portion and a first support arm extending from the first support portion, the first support portion configured to interface with a first surface of the first vertebral body;
      a second member including a second support portion and a second support arm extending from the second support portion, the second support portion configured to interface with a second surface of the second vertebral body;
      a first engagement member having an oblong shaped cam outer surface, the engagement member positioned between the first support portion and the second support portion and between the first support arm and the second support arm, the engagement member being rotatable such that the oblong shaped cam outer surface directly engages inner surfaces of the respective first support portion and the second support portion to move the first support portion relative to the second support portion so that the expandable member is moveable between the collapsed position and the expanded position; and
      a second engagement member including retractable blades, the retractable blades extending directly from the oblong shaped cam outer surface.

2. The system of claim 1, wherein the engagement member rotates to fixate the first support portion to the first vertebral body and to fixate the second support portion to the second vertebral body.

3. The system of claim 1, wherein the second engagement member is configured to move from a retracted position and a deployed position, in the deployed position, the second engagement member extends into the first and second vertebral body to supplementally fixate the first and second members in the expanded position.

4. The system of claim 3, wherein the retractable blades retract from the oblong shaped cam outer surface.

5. The system of claim 1, wherein the first engagement member comprises a cam sized to expand the expandable member upon the cam being rotated.

6. The system of claim 1, wherein the retractable blades are configured to retract directly from the oblong shaped cam outer surface.

7. The system of claim 1, wherein the inner surfaces of the respective first support portion and the second support portion extend parallel relative to each other.

8. A system for supporting a first vertebral body and a second vertebral body, comprising:
   a first member including a first support portion and a first support arm extending from the first support portion, the first portion configured to interface with a first surface of the first vertebral body;
   a second member including a second support portion and a second support arm extending from the second support portion, the second support portion configured to interface with a second surface of the second vertebral body, the first member moveable relative to the second member between a collapsed position and an expanded position;
   a first engagement member having an outer surface defining an oblong shaped cam, the first engagement member positioned between the first member and the second member, the first engagement member being rotatable such that the outer surface directly engages inner surfaces of the respective first support portion and the second support portion to move the first member relative to the second member between the collapsed position and the expanded position; and
   a second engagement member including retractable blades, the retractable blades configured to move from a retracted position and a deployed position, in the deployed position, the retractable blades extend directly from the outer surface of the oblong shaped cam and extend into the first and second vertebral body so as to maintain the first and second members in the expanded position.

9. The system of claim 8, wherein, in the deployed position, the second engagement member extends directly from the first engagement member and through the first support portion of the first member.

10. The system of claim 8, wherein the second engagement member is configured to fixate the first and second members to the first vertebral body and the second vertebral body, respectively, while also maintaining the first and second members in the expanded position.

11. The system of claim 8, wherein, in the collapsed position, the first member and the second member are sized to be positioned between the first vertebral body and the second vertebral body.

12. The system of claim 8, upon the first and second members being positioned between the first and second vertebral bodies, the first engagement member is actuated to move the first and second members to the expanded position and to fixate the first and second members to the respective first and second vertebral bodies.

13. The system of claim 8, wherein the first engagement member is positioned between the first and second support portions and between the first and second support arms such that the first engagement member engages the first and second support portions in the collapsed position and the expanded positions.

14. The system of claim 8, wherein the retractable blades are configured to retract directly from the outer surface of the oblong shaped cam.

15. The system of claim 8, wherein the inner surfaces of the respective first support portion and the second support portion extend parallel relative to each other.

* * * * *